(12) United States Patent
Stern et al.

(10) Patent No.: US 11,390,900 B2
(45) Date of Patent: Jul. 19, 2022

(54) ANTIMICROBIAL CARTRIDGES AND PROCESSES FOR MULTIPLEXED ANTIMICROBIAL SUSCEPTIBILITY TESTING

(71) Applicant: SELUX DIAGNOSTICS, INC., Charlestown, MA (US)

(72) Inventors: Eric Stern, Jamaica Plain, MA (US); Kelly Flentie, Jamaica Plain, MA (US); Aleksandar Vacic, Cambridge, MA (US); Frederick P. Floyd, Boston, MA (US); Sarah A. Scott, Medford, MA (US)

(73) Assignee: SELUX DIAGNOSTICS, INC., Charlestown, MA (US)

( * ) Notice: Subject to any disclaimer, the term of this patent is extended or adjusted under 35 U.S.C. 154(b) by 226 days.

(21) Appl. No.: 16/435,184

(22) Filed: Jun. 7, 2019

(65) Prior Publication Data

US 2019/0376111 A1 Dec. 12, 2019

Related U.S. Application Data

(60) Provisional application No. 62/682,571, filed on Jun. 8, 2018.

(51) Int. Cl.
| | | |
|---|---|---|
| *C12Q 1/18* | (2006.01) | |
| *C12Q 1/04* | (2006.01) | |
| *B01L 3/00* | (2006.01) | |
| *C12Q 1/02* | (2006.01) | |

(52) U.S. Cl.
CPC .............. *C12Q 1/18* (2013.01); *B01L 3/5085* (2013.01); *C12Q 1/025* (2013.01); *C12Q 1/04* (2013.01); *C12Q 2545/101* (2013.01); *C12Q 2547/10* (2013.01)

(58) Field of Classification Search
CPC ....................................................... C12Q 1/18
See application file for complete search history.

(56) References Cited

U.S. PATENT DOCUMENTS

| | | |
|---|---|---|
| 4,153,512 A | 5/1979 | Messner et al. |
| 4,453,220 A | 6/1984 | Flegal et al. |
| 4,530,806 A | 7/1985 | Melchior |
| 2005/0048575 A1 | 3/2005 | Coassin et al. |
| 2008/0318268 A1 | 12/2008 | Olson et al. |
| 2010/0099137 A1 | 4/2010 | Taintor |
| 2011/0159515 A1 | 6/2011 | Stimson |
| 2012/0009558 A1 | 1/2012 | Armstrong et al. |
| 2012/0329675 A1 | 12/2012 | Olson et al. |
| 2015/0024436 A1 | 1/2015 | Eberhart et al. |
| 2017/0058314 A1 | 3/2017 | Zhang et al. |
| 2017/0211121 A1 | 7/2017 | Stern et al. |
| 2017/0340609 A1 | 11/2017 | Alam |
| 2018/0088141 A1 | 3/2018 | Vacic et al. |

FOREIGN PATENT DOCUMENTS

| | | |
|---|---|---|
| EP | 3301454 A1 | 4/2018 |
| WO | 90008196 A1 | 7/1990 |
| WO | 2014142786 A1 | 9/2014 |
| WO | 2016037051 A1 | 3/2016 |
| WO | 2016137341 A1 | 9/2016 |
| WO | 2016161022 A2 | 10/2016 |
| WO | 2017185012 A1 | 10/2017 |

OTHER PUBLICATIONS

International Preliminary Search Report for International application No. PCT/US2018/016708, dated Aug. 6, 2019, 8 pages.
International Search Report and Written Opinion for International application No. PCT/US2019/036129, dated Sep. 23, 2019, 14 pages.
Tang, Y., et al., "Rapid Antibiotic Suceptibility Testing in a Microfluidic pH Sensor", Analytical Chemistry, 85 (5):2787-2794 (2013).
Sun, W., et al., "Rapid antimicrobial susceptibility test for identification of new therapeutics and drug combinations against multidrug-resistant bacteria", Emerging Microbes & Infections 5(1):1-11 (2016).
Zhanel, G.G., et al., "Ceftazidime-Avibactam: a Novel Cephalosporin/ β-lactamase Inhibitor Combination", Drugs 73:159-177 (2013).

*Primary Examiner* — Albert M Navarro
(74) *Attorney, Agent, or Firm* — Goodwin Procter LLP

(57) ABSTRACT

The present invention provides, among other things, cartridges for multiplexed antimicrobial susceptibility testing (AST), single cartridges useful for both AST and quality control of AST, and systems and methods relating thereto.

21 Claims, 19 Drawing Sheets

FIGURE 2A

BROAD SPECTRUM MASTER

RESERVED FOR CONTROL WELLS ON TARGET

| | 1 | 2 | 3 | 4 | 5 | 6 | 7 | 8 | 9 | 10 | 11 | 12 |
|---|---|---|---|---|---|---|---|---|---|---|---|---|
| A | TGC 0.390625 | TGC 1.5625 | TGC 6.25 | TGC 25 | TGC 100 | SAM 25/12.5 | SAM 100/50 | SAM 400/50 | | | | |
| B | SXT 12.5 | SXT 50 | SXT 200 | SXT 800 | LVX 6.25 | LVX 25 | LVX 100 | DOX 12.5 | DOX 50 | DOX 200 | | |
| C | CIP 0.78125 | CIP 3.125 | CIP 12.5 | CIP 50 | CRO 12.5 | CRO 50 | CRO 200 | | | | | |
| D | AMK 12.5 | AMK 50 | AMK 200 | AMK 800 | CZA 25/50 | CZA 50/50 | CZA 100/50 | CZA 200/50 | CZA 400/50 | | | |
| E | AMP 1.5625 | AMP 6.25 | AMP 25 | AMP 100 | AMP 400 | MXF 12.5 | MXF 50 | MXF 200 | | | | |
| F | GEN 3.125 | GEN 12.5 | GEN 50 | GEN 200 | FOX 25 | FOX 100 | FOX 400 | | | | | |
| G | TET 3.125 | TET 12.5 | TET 50 | TET 200 | MNC 12.5 | MNC 50 | MNC 200 | | | | | |
| H | TOB 3.125 | TOB 12.5 | TOB 50 | TOB 200 | NIT 100 | NIT 400 | NIT 1600 | | | | | |

GRAM POSITIVE MASTER

| | 1 | 2 | 3 | 4 | 5 | 6 | 7 | 8 | 9 | 10 | 11 | 12 |
|---|---|---|---|---|---|---|---|---|---|---|---|---|
| A | DAP 0.78125 | DAP 3.125 | DAP 12.5 | DAP 50 | VAN 6.25 | VAN 25 | VAN 100 | VAN 400 | | | | RESERVED FOR CONTROL WELLS ON TARGET |
| B | OXA 0.390625 | OXA 1.5625 | OXA 6.25 | OXA 25 | OXA 100 | LNZ 6.25 | LNZ 25 | LNZ 100 | | | | |
| C | CLI 0.78125 | CLI 3.125 | CLI 12.5 | CLI 50 | CLI 200 | AZM 6.25 | AZM 25 | AZM 100 | GEN H. 6250 | | | |
| D | CPT 0.390625 | CPT 1.5625 | CPT 6.25 | CPT 25 | CPT 100 | ERY 6.25 | ERY 25 | ERY 100 | MUP H. 3200 | | | |
| E | PEN 0.78125 | PEN 3.125 | PEN 12.5 | PEN 50 | PEN 200 | TDZ 15625 | TDZ 625 | TDZ 25 | STP H. 12500 | | | |
| F | RIF 6.25 | RIF 25 | RIF 100 | RIF 400 | QNP/DFP 3.125 | QNP/DFP 12.5 | QNP/DFP 50 | CLI/ERY 6.25/12.5 | CLI/ERY 6.25/50 | | | |
| G | | | | | | | | | | | | |
| H | | | | | | | | | | | | |

FIGURE 2A (continued)

GRAM NEGATIVE MASTER

| | 1 | 2 | 3 | 4 | 5 | 6 | 7 | 8 | 9 | 10 | 11 | 12 |
|---|---|---|---|---|---|---|---|---|---|---|---|---|
| A | TZP 50/50 | TZP 100/50 | TZP 200/50 | TZP 400/50 | TZP 800/50 | TZP 1600/50 | ATM 25 | ATM 100 | ATM 400 | | | RESERVED FOR CONTROL WELLS ON TARGET |
| B | AMC 25/12.5 | AMC 100/50 | AMC 400/200 | CFX 25 | CFX 100 | CFX 400 | FEP 100 | FEP 400 | FEP/QLV 125/125 | | | |
| C | CFZ 6.25 | CFZ 25 | CFZ 100 | CFZ 400 | FEP 6.25 | FEP 25 | CTX 200 | CTX 800 | CTX/QLV 6.25/50 | | | |
| D | CST 1.5625 | CST 6.25 | CST 25 | CST 100 | CTX 12.5 | CTX 50 | CAZ 100 | CAZ 400 | CAZ/CLB 6.25/50 | | | |
| E | IMP 3.125 | IMP 12.5 | IMP 50 | IMP 200 | CAZ 6.25 | CAZ 25 | DOR 25 | DOR 100 | | | | |
| F | MEM 1.5625 | MEM 6.25 | MEM 25 | MEM 100 | DOR 1.5625 | DOR 6.25 | CPD 6.25 | CPD 6.25 | | | | |
| G | ERT 0.78125 | ERT 3.125 | ERT 12.5 | ERT 50 | ERT 200 | CPD 6.25 | C/T 200/50 | | | | | |
| H | C/T 3.125/50 | C/T 6.25/50 | C/T 12.5/50 | C/T 25/50 | C/T 50/50 | C/T 100/50 | | | | | | |

Combo Target Wells

| | 1 | 2 | 3 | 4 | 5 | 6 | 7 | 8 | 9 | 10 | 11 | 12 |
|---|---|---|---|---|---|---|---|---|---|---|---|---|
| A | Combo A1 4μL | Combo A1 8μL | Combo A2 4μL | Combo A2 8μL | Combo A3 4μL | Combo A3 8μL | Combo A4 4μL | Combo A4 8μL | Combo A5 4μL | Combo A5 8μL | Combo A6 4μL | Combo A6 8μL |
| B | Combo B1 4μL | Combo B1 8μL | Combo B2 4μL | Combo B2 8μL | Combo B3 4μL | Combo B3 8μL | Combo B4 4μL | Combo B4 8μL | Combo B5 4μL | Combo B5 8μL | Combo B6 4μL | Combo B6 8μL |
| C | Combo C1 4μL | Combo C1 8μL | Combo C2 4μL | Combo C2 8μL | Combo C3 4μL | Combo C3 8μL | Combo C4 4μL | Combo C4 8μL | Combo C5 4μL | Combo C5 8μL | Combo C6 4μL | Combo C6 8μL |
| D | Combo D1 4μL | Combo D1 8μL | Combo D2 4μL | Combo D2 8μL | Combo D3 4μL | Combo D3 8μL | Combo D4 4μL | Combo D4 8μL | Combo D5 4μL | Combo D5 8μL | Combo D6 4μL | Combo D6 8μL |
| E | Combo E1 4μL | Combo E1 8μL | Combo E2 4μL | Combo E2 8μL | Combo E3 4μL | Combo E3 8μL | Combo E4 4μL | Combo E4 8μL | Combo E5 4μL | Combo E5 8μL | Combo E6 4μL | Combo E6 8μL |
| F | Combo F1 4μL | Combo F1 8μL | Combo F2 4μL | Combo F2 8μL | Combo F3 4μL | Combo F3 8μL | Combo F4 4μL | Combo F4 8μL | Combo F5 4μL | Combo F5 8μL | Combo F6 4μL | Combo F6 8μL |
| G | Combo G1 4μL | Combo G1 8μL | Combo G2 4μL | Combo G2 8μL | Combo F3 4μL | Combo G3 8μL | Combo G4 4μL | Combo G4 8μL | Combo G5 4μL | Combo G5 8μL | Combo G6 4μL | Combo G6 8μL |
| H | Combo H1 4μL | Combo H1 8μL | Combo H2 4μL | Combo H2 8μL | Combo H3 4μL | Combo H3 8μL | Combo H4 4μL | Combo H4 8μL | Combo H5 4μL | Combo H5 8μL | Combo H6 4μL | Combo H6 8μL |

Combo Target Wells

| | 13 | 14 | 15 | 16 | 17 | 18 | 19 | 20 | 21 | 22 | 23 | 24 |
|---|---|---|---|---|---|---|---|---|---|---|---|---|
| | Combo A7 4μL | Combo A7 8μL | Combo A8 4μL | Combo A8 8μL | Combo A9 4μL | Combo A9 8μL | Combo A10 4μL | Combo A10 8μL | Combo A11 4μL | Combo A11 8μL | | |
| | | | | | | | | | | | | |
| | Combo B7 4μL | Combo B7 8μL | Combo B8 4μL | Combo B8 8μL | Combo B9 4μL | Combo B9 8μL | Combo B10 4μL | Combo B10 8μL | Combo B11 4μL | Combo B11 8μL | | |
| | | | | | | | | | | | | |
| | Combo C7 4μL | Combo C7 8μL | Combo C8 4μL | Combo C8 8μL | Combo C9 4μL | Combo C9 8μL | Combo C10 4μL | Combo C10 8μL | Combo C11 4μL | Combo C11 8μL | | |
| From Fig. 10A | | | | | | | | | | | | |
| | Combo D7 4μL | Combo D7 8μL | Combo D8 4μL | Combo D8 8μL | Combo D9 4μL | Combo D9 8μL | Combo D10 4μL | Combo D10 8μL | Combo D11 4μL | Combo D11 8μL | | |
| | | | | | | | | | | | | |
| | Combo E7 4μL | Combo E7 8μL | Combo E8 4μL | Combo E8 8μL | Combo E9 4μL | Combo E9 8μL | Combo E10 4μL | Combo E10 8μL | Combo E11 4μL | Combo E11 8μL | | |
| | | | | | | | | | | | | |
| | Combo F7 4μL | Combo F7 8μL | Combo F8 4μL | Combo F8 8μL | Combo F9 4μL | Combo F9 8μL | Combo F10 4μL | Combo F10 8μL | Combo F11 4μL | Combo F11 8μL | | |
| | | | | | | | | | | | | |
| | Combo G7 4μL | Combo G7 8μL | Combo G8 4μL | Combo G8 8μL | Combo G9 4μL | Combo G9 8μL | Combo G10 4μL | Combo G10 8μL | Combo G11 4μL | Combo G11 8μL | | |
| | | | | | | | | | | | | |
| | Combo H7 4μL | Combo H7 8μL | Combo H8 4μL | Combo H8 8μL | Combo H9 4μL | Combo H9 8μL | Combo H10 4μL | Combo H10 8μL | Combo H11 4μL | Combo H11 8μL | | |
| | | | | | | | | | | | | |

ANTIMICROBIAL CARTRIDGES AND PROCESSES FOR MULTIPLEXED ANTIMICROBIAL SUSCEPTIBILITY TESTING

REFERENCE TO RELATED APPLICATIONS

This application claims the benefit of priority to U.S. Provisional Patent Application No. 62/682,571, filed Jun. 8, 2018, the entire disclosure of which is hereby incorporated by reference.

FIELD

The present invention relates generally to antimicrobial susceptibility testing and more specifically to devices and methods for rapid antimicrobial susceptibility testing of clinical samples.

BACKGROUND

Current broth dilution antimicrobial susceptibility test (AST) methods utilize individual cartridges with less than 130 reservoirs pre-filled with antimicrobial compounds supplied at the desired testing concentrations. Antimicrobial compounds may exhibit poor stability in solution. As a result, cartridges comprising dried antimicrobial compounds are utilized in laboratory practice because they can be shipped and stored at room temperature without antimicrobial degradation. Dried cartridges are designed for reconstitution with aqueous solutions. In order to prevent cross contamination, the AST method relies on transferring the same concentration of a microorganism into each reservoir, such that each cartridge is designed for use with a single microorganism under test. Moreover, each cartridge comes with a preset layout and range of concentration of antimicrobial compounds which limits scope of exploring newer drug concentrations or types for a variety of patient samples. There is therefore a need for more versatile cartridge systems for robust multiplex assay designs. Furthermore, there is a need for increasing numbers of reservoirs per patient cartridge in order to test the larger numbers of antimicrobials available for drug-resistant pathogens.

SUMMARY

In one aspect, this disclosure provides a cartridge that can be used for both antimicrobial susceptibility testing of microorganisms derived from human samples and quality control (QC), reducing the costs and complexity of performing periodic regular quality control of AST systems. Cartridges according to this aspect of the disclosure can include a first plurality of reservoirs comprising at least 8, 10, 12, 14, 16, 18, 20, 22 or 25 different antimicrobials, each antimicrobial being present at a plurality of different amounts or concentrations across different reservoirs, thereby defining a dilution series. Cartridges according to this aspect of the disclosure can also include an arrangement of a plurality of these dilution series into "QC blocks," such that each block comprises a plurality of antimicrobials that may utilize the same QC microorganism. In various embodiments, the cartridge includes at least 96 reservoirs, or at least 384 reservoirs. The dilution series can, in some cases, include a plurality of concentrations defining a range of predicted minimum inhibitory concentrations (MIC) of the antimicrobial for a patient sample and a quality control (QC) organism, and each dilution series may, variously, include at least one concentration above or below the range of predicted MICs of the antimicrobial for the patient sample and the QC organism. In some cases, a plurality of antimicrobial dilution series comprise sufficient dilution extents to include a minimum inhibitory concentration (MIC) of the indicated QC organism. Each dilution series may include at least one concentration below the lower of a) a lowest clinical breakpoint for which the antimicrobial has an indication or b) the lower end of a QC range for the indicated QC microorganism. The lowest concentration may be half the concentration of a second-lowest concentration. The lowest concentration may be less than half the concentration of a second-lowest concentration. The lowest concentration may be greater than half the concentration of a second-lowest concentration. Each dilution series may include at least one concentration above the higher of the highest clinical breakpoint for which the antimicrobial has an indication and the higher end of the QC range for the organism of the QC block. The highest concentration may be double that of the second-highest concentration. The highest concentration may be less than double that of the second-highest concentration. The highest concentration may be greater than double that of the second-highest concentration.

In some cases, the range of predicted MICs of the antimicrobial for a patient sample are not identical to the range of predicted MICs of the antimicrobial for a QC organism. Two or more reservoirs of the cartridge may optionally comprise a sufficient quantity of an antimicrobial compound to inhibit the growth of a plurality of gram-negative microorganisms. The antimicrobial compound present at high concentrations may be a carbapenem. The cartridge optionally includes at least one sufficient growth reservoir in each QC block of the panel. In some cases, the cartridge includes orthogonal axes defining first and second directions; in these cases, when the dilution series for the various antimicrobials are oriented in the first direction (e.g., vertically), inoculation of the cartridge may be specified to occur in the same direction (i.e., the first direction) or in the second direction. In some cases, a plurality of the dilution series may be oriented in the first direction and each QC block may comprise a plurality of dilution series which are adjacent to each other across the second direction. The dilution series for each of the plurality of antimicrobials may be oriented in the first direction, and a microorganism sample may be inoculated in the first direction.

Continuing with this aspect of the disclosure, the cartridge may include one or more antimicrobials selected from the list consisting of: Amikacin, Amikacin-fosfomycin, Amoxicillin, Amoxicillin-clavulanate, Ampicillin, Ampicillin-sulbactam, Azithromycin, Azithromycin-Avibactam, Azlocillin, Aztreonam, Aztreonam-avibactam, Besifloxacin, Biapenem, Cadazolid, Carbenicillin, Cefaclor, Cefamandole, Cefazolin, Cefdinir, Cefditoren, Cefepime, Cefepime-tazobactam, Cefetamet, Cefiderocol, Cefixime, Cefmetazole, Cefonicid, Cefoperazone, Cefotaxime, Cefotetan, Cefoxitin, Ceftolozane-tazobactam, Cefpodoxime, Cefprozil, Ceftaroline, Ceftaroline-avibactam, Ceftazidime, Ceftazidime-avibactam, Ceftibuten, Ceftizoxime, Ceftobiprole, Ceftolozane-tazobactam, Ceftriaxone, Cefuroxime, Cephalothin, Chloramphenicol, Cinoxacin, Ciprofloxacin, Clarithromycin, Clinafloxacin, Clindamycin, Colistin, Dalbavancin, Daptomycin, Delafloxacin, Dirithromycin, Doripenem, Doxycycline, Enoxacin, Eravacycline, Ertapenem, Erythromycin, Faropenem, Fidaxomicin, Finafloxacin, Fleroxacin, Fosfomycin, Fusidic acid, Garenoxacin, Gatifloxacin, Gemifloxacin, Gentamicin, Gepotidacin, Grepafloxacin, Iclaprim, Imipenem, Imipenem-Relebactam, Kanamycin, Lefamulin, Levofloxacin, Levonadifloxacin, Linezolid, Linopristin-flopristin, Lomefloxacin, Loracarbef, Mecillinam, Meropenem, Methicillin, Mezlocillin, Minocycline, Moxalactam, Moxifloxacin, Nafcillin, Nalidixic acid, Netilmicin, Nitrofurantoin, Norfloxacin, Ofloxacin, Omadacycline, Oritavancin, Oxacillin, Penicillin, Piperacillin, Piperacillin-tazobactam, Plazomicin, Polymyxin B, Quinupristin-dalfopristin, Razupenem, Rifampin, Solithromycin, Sparfloxacin, Sulfisoxazole, Sulopenem, Tedizolid, Teicoplanin, Televancin, Telithromycin, Tetracycline, Ticarcillin, Ticarcillin-clavulanate, Tigecycline, Tobramycin, Trimethoprim, Trimethoprim-sulfamethoxazole, Trospectomycin, Vancomycin, Aculeacin A, Amphotericin B, Caspofungin, Clotrimazole, Fluconazole, Flucytosine, 5-Fluorocytosine, Griseofulvin, Itraconazole, Ketoconazole, Nystatin, Sordarin, Terbinafine, Vaborbactam-meropenem, Voriconazole and a salt or hydrate form thereof. A QC organism for an antimicrobial can include, in various embodiments, *Staphylococcus aureus* ssp. *aureus* (ATCC 29213); *Enterococcus faecalis* (ATCC 29212); *Escherichia coli* (ATCC 25922); *Klebsiella pneumoniae* ssp. *pneumoniae* (ATCC 700603); *Klebsiella pneumoniae* (ATCC BAA2814); *Pseudomonas aeruginosa* (ATCC 27853); *E. faecalis* (ATCC 51299); *S. aureus* (BAA-1708); *S. aureus* (BAA-977); *S. aureus* (ATCC 43300); *Streptococcus pneumoniae* (ATCC 49619) and *Trichothecium plasmoparae* (ATCC 13353). Exemplary cartridge layouts according to this aspect of the invention are presented in FIGS. 2B and 2C.

In another aspect, the disclosure relates to a method of performing AST using a cartridge comprising at least 96 or at least 384 reservoirs and at least 8, 10, 12, 14, 16, 18, 20, 25 or 30 unique antimicrobials, including without limitation a cartridge according to the aspect of the disclosure presented above. The method includes directing a user to select to perform clinical or QC sample testing in the system software. In some cases, if QC sample testing is selected, the method includes directing the user to load two or more different QC organisms together with the cartridge into the system, inoculating the two or more different QC organisms into the cartridge, incubating the cartridge under conditions promoting microorganism growth for a period between 2 and 18 hours, and performing one or more AST assays to determine the MIC for the QC organisms for antimicrobials on the cartridge. In an embodiment wherein one or more of the AST assays are not initiated until a sufficient growth assay threshold is achieved, the sufficient growth assay comprises one or more optical measurements of one or more inoculated reservoirs comprising a metabolic probe and no antimicrobial, the sufficient assay threshold is defined as a pre-determined optical measurement value, and the sufficient assay threshold may be different for different organisms. The metabolic probe may comprise resazurin and the optical measurement may comprise a fluorescent measurement. One or more AST assays may comprise a metabolic assay and surface binding assay. A plurality of reservoirs on the cartridge may be interrogated for growth between 1 and 3 times before the MIC is determined.

In another aspect, the disclosure relates to a method of performing AST or providing QC for an AST with a cartridge comprising at least 96 or at least 384 reservoirs and at least 8 unique antimicrobials, each present in a plurality of concentrations defining a dilution series that spans both an expected clinical breakpoint range and an expected QC organism breakpoint range. The method includes inoculating the cartridge with either a patient-derived sample comprising a microorganism or at least one QC organism for an antimicrobial present on the cartridge, incubating the cartridge under conditions promoting microorganism growth for a period between 2 and 24 hours, and performing one or more assays to determine, for the test sample or QC organism, a minimum inhibitory concentration (MIC) for a plurality of antimicrobials on the cartridge. If the cartridge is inoculated with a patient-derived sample, the step of determining the MICs for the test sample comprises comparing microorganism growth at antimicrobial concentrations within the clinical breakpoint range. If the cartridge is inoculated with a QC organism, the step of determining the MICs for the QC organism comprises comparing QC organism growth at antimicrobial concentrations within the expected QC range. In some cases, each antimicrobial dilution series is replicated two or more times and the cartridge is inoculated with two or more patient derived samples. If a gram-negative microorganism is inoculated, at least two reservoirs of the cartridge are inoculated with different amounts or concentrations of the microorganisms than the dilution series receive, and the concentration may be higher than the other reservoirs of the cartridge. The cartridge is then incubated under conditions promoting microorganism growth for a period between 2 and 24 hours, and one or more assays to determine the MIC for the patient-derived sample or QC organism(s) for a plurality of antimicrobials on the cartridge is performed. In some cases, a plurality of reservoirs on the cartridge are interrogated for growth between 1 and 5 times before the MIC is determined. Where QC organism(s) are used, the method also optionally includes comparing the MIC of the antimicrobial for the QC organism to a reference range and, if the MIC is not within the reference range, signaling to a user of the AST system that the MIC for the antimicrobial is out of range.

In another aspect, the disclosure relates to a method of performing AST with a multiplex cartridge (e.g., comprising at least 96 or at least 384 reservoirs and at least 8 unique antimicrobials, each present in dilution series replicated two or more times), comprising the steps described above. In some embodiments of any of the foregoing aspects of the disclosure, no more than 10% of the reservoirs are interrogated to assess microbial growth prior to the MIC-determining assays.

In yet another aspect, the disclosure relates to a cartridge for multiplex AST testing, comprising a plurality of reservoirs organized into a plurality of identical arrays of reservoirs, each array of reservoirs defining an AST panel and comprising a plurality of antimicrobials at a plurality of concentrations. Each array of reservoirs can, in some cases, include a plurality of reservoirs comprising different amounts of an antimicrobial and defining a dilution series for the antimicrobial, and at least one well that does not include an antimicrobial. Alternatively or additionally, the cartridge can include at least one removable covering sealing at least one array of reservoirs, such as a membrane or cover; some embodiments utilize a plurality of removable coverings, each removable covering sealing an array of reservoirs.

In another embodiment, this disclosure relates to a kit for performing antimicrobial susceptibility testing (AST) comprising a cartridge according to this disclosure. This kit may be perform a) an AST method comprising the steps of: inoculating the cartridge with a patient derived sample, assessing, based on a comparison of cell growth in differing antimicrobial concentrations, one of a minimum inhibitory concentration (MIC) of an antimicrobial, and a susceptibility to an antimicrobial and/or b) a quality control (QC) method comprising the steps of: inoculating the cartridge with at least one QC organism specified for an antimicrobial present on the cartridge, and assessing, based on a comparison of cell growth in differing antimicrobial concentrations and a normal range for the QC organism, whether a MIC of an antimicrobial is within the normal range for the QC organism. This kit may be automated. This kit may comprise dilution series oriented in the same direction such that the inoculation of the cartridge with the patient derived sample does not cause contamination within the cartridge. This kit may also comprise a plurality of QC organisms which are used to provide quality control for the antimicrobials present on the cartridge, wherein a plurality of different wells in the cartridge are inoculated with the plurality of QC organisms simultaneously The foregoing listing is intended to exemplify, rather than limit, the aspects and embodiments of the present disclosure, and those of skill in the art will appreciate that these aspects and embodiments may be modified in ways currently known in the art without departing from the spirit of this disclosure.

BRIEF DESCRIPTION OF THE DRAWINGS

The above and further features will be more clearly appreciated from the following detailed description when taken in conjunction with the drawings. The drawings are however for illustration purpose only, not for a limitation.

FIG. 2A depicts layout of antimicrobials on a three-plate master cartridge comprising an antimicrobial panel known to act against both gram positive and gram-negative bacteria; an antimicrobial panel known to against gram negative bacteria; and an antimicrobial panel known to be active against gram positive bacteria. Each antimicrobial is depicted by a three-letter abbreviation of the convention.

FIG. 2B depicts the layout of an exemplary 384-well cartridge for an AST system for gram positive bacteria and FIG. 2C depicts the layout of an exemplary 384-well cartridge for gram negative bacteria. Each cartridge includes a plurality of dilution series for multiple antimicrobial agents; each dilution series also includes a prescribed quality control organism for the antimicrobial. In the figures, for each dilution series, the antimicrobial is referenced on the top line by the three-letter code presented in Table 9, and the quality control organism is specified on the middle line. The concentration of the antimicrobial in each well is depicted on the bottom line for the series. Darkened concentration values denote concentrations expected to be outside of the MIC range of the antimicrobial for the quality control organism, while lighter values denote concentrations expected to be in-range. The design of each plate with antibiotic dilution series clustered in vertical blocks enables multiple quality control organisms to be loaded and processed in a single run. FIG. 2D depicts the layout of an exemplary 384-well cartridge for an AST system for gram negative bacteria and FIG. 2E depicts the layout of an exemplary 384-well cartridge for gram positive bacteria.

FIG. 5 depicts the final layout of a patient cartridge 384 well comprising antimicrobials against gram negative bacteria.

FIG. 6 depicts the final layout of a patient cartridge 384 well comprising antimicrobials against gram positive bacteria.

Figure 9:
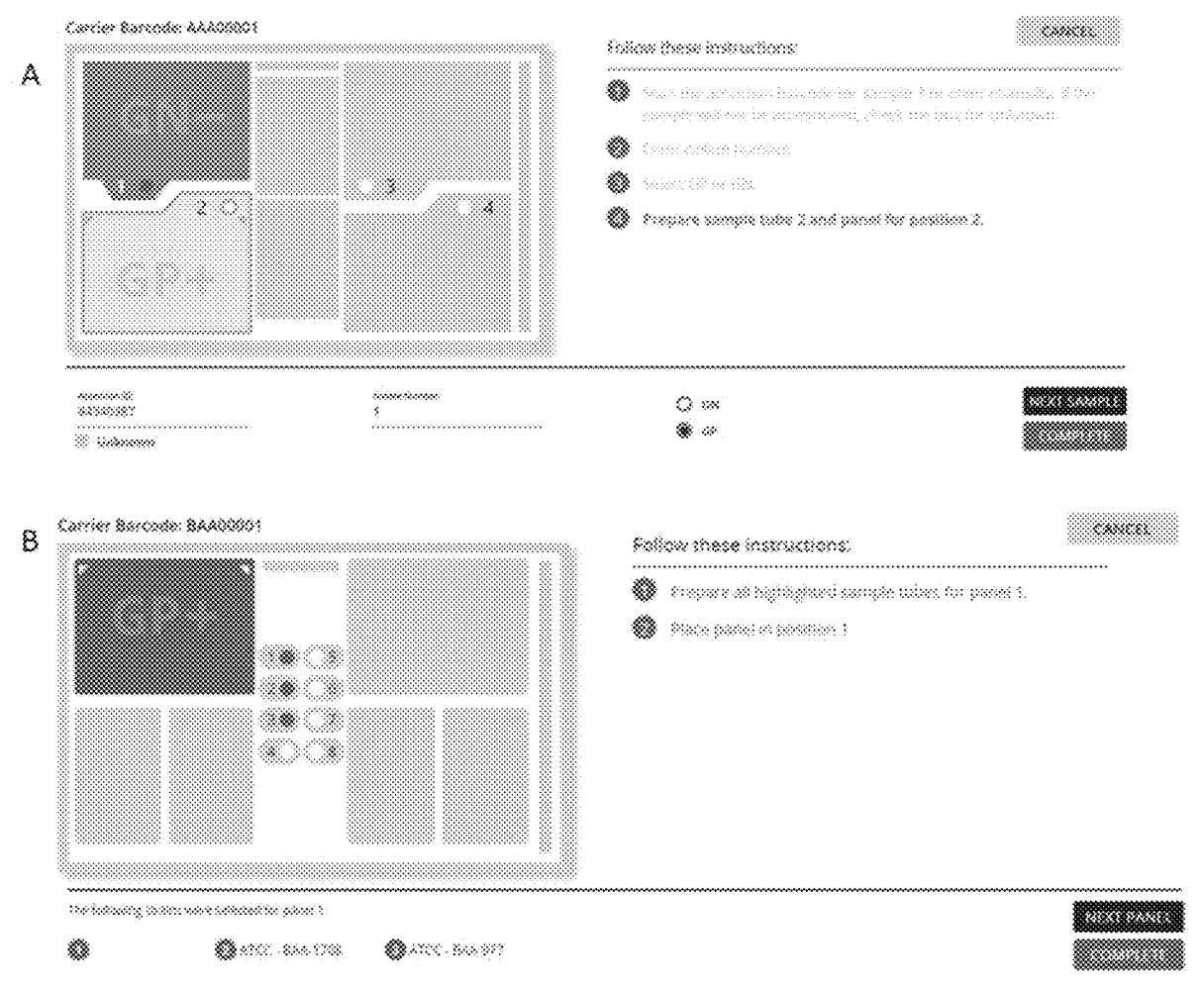

FIG. 9 depicts instructions and sample handling for Gram positive and Gram negative specimens according to the embodiments of this disclosure.

FIG. 10A-B depicts patient cartridge Broad Spectrum plate layout.

FIG. 11A-B depicts patient Cartridge layout of Gram positive or Gram negative antimicrobials.

DEFINITIONS

Figure 1:
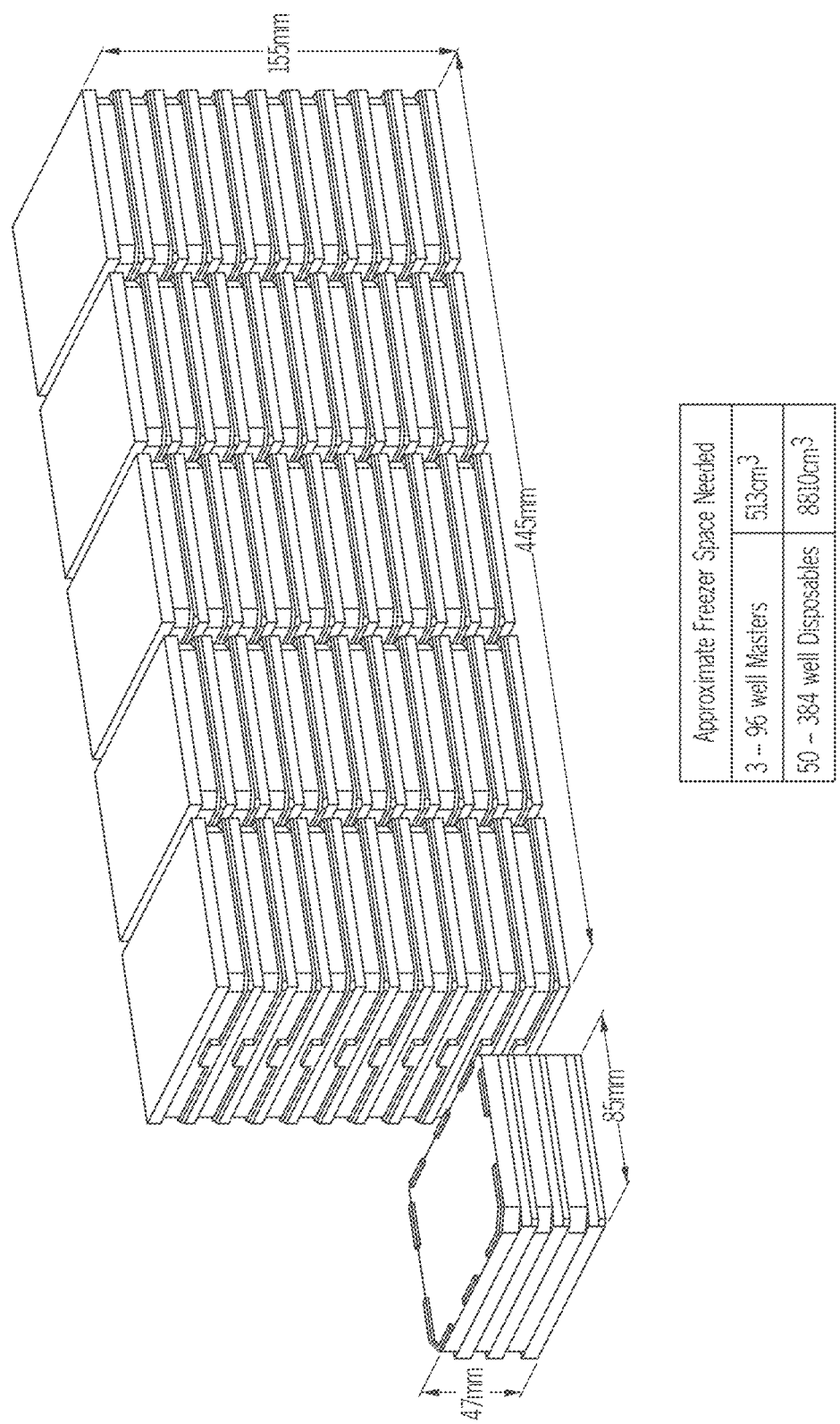
FIG. 1 depicts space requirements for AST master cartridge versus available AST assay plates. Compared to the 50 assay plates, master cartridge of three 96 well plates require considerably less storage space.

The patent and scientific literature referred to herein establishes knowledge that is available to those of skill in the art. The issued U.S. patents, allowed applications, published foreign applications, and references that are cited herein are hereby incorporated by reference to the same extent as if each was specifically and individually indicated to be incorporated by reference.

As used herein, the recitation of a numerical range for a variable is intended to convey that the invention may be practiced with the variable equal to any of the values within that range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values$\geq 0$ and $\leq 2$ if the variable is inherently continuous.

As used herein, unless specifically indicated otherwise, the word "or" is used in the inclusive sense of "and/or" and not the exclusive sense of "either/or."

In order for the present invention to be more readily understood, certain terms are first defined below. Additional definitions for the following terms and other terms are set forth throughout the specification.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal are transgenic animals, genetically-engineered animals, and/or a clone.

Antimicrobial: As used herein an antimicrobial refers to an agent that kills (microbicidal), attenuates (microbistatic) or inhibits the function of a microorganism. An antimicrobial can be a chemical compound, a biological product, such as a peptide, protein, an antibody or a nucleic acid, or a small molecule. It may be naturally occurring product or a synthetic product.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Clinical breakpoint ranges for various antimicrobials are provided in the Clinical and Laboratory Standards Institute (CLSI) publication "M100—Performance Standards for Antimicrobial Susceptibility testing," the FDA website at https://www.fda.gov/Drugs/DevelopmentApprovalProcess/ DevelopmentResources/ucm575163.htm, and the EUCAST website http://www.eucast.org/clinical_breakpoints/. This set of values determines the interpretive criteria of the MIC result determined by the AST assay. All MIC values up to and including the susceptible value will be reported as Susceptible to the clinical floor. For MICs above the Susceptible value, depending on the antimicrobial and species under test, values of Intermediate, Susceptible Dose-Dependent, and Resistant may be reported. For example, for ciprofloxacin and Enterobacteriaceae, the Susceptible MIC cutoff is 1 µg/mL; an MIC of 2 µg/mL is reported as Intermediate; and all MICs above 4 µg/mL are reported as Resistant.

Clinically relevant dilution range: As used herein, a "clinically relevant dilution range" is the clinical breakpoint range plus two dilutions below the Susceptible value and one dilution above the Resistant value. For example, for ciprofloxacin and Enterobacteriaceae, the Susceptible MIC cutoff is 1 µg/mL and all MICs above 4 µg/mL are reported as Resistant, so the clinically relevant dilution range would span from 0.25 µg/mL to 8 µg/mL.

Delivery: As used herein, the term "delivery" encompasses both local and systemic delivery. For example, delivery of antimicrobial encompasses situations in which an antimicrobial is delivered to a target tissue and the encoded protein is expressed and retained within the target tissue (also referred to as "local distribution" or "local delivery"), and situations in which an antimicrobial is delivered to a target tissue and the encoded protein is expressed and secreted into patient's circulation system (e.g., serum) and systematically distributed and taken up by other tissues (also referred to as "systemic distribution" or "systemic delivery").

Dilution range: As used herein, dilution range refers to range of serial dilutions (or "doubling" dilutions) for a given antimicrobial, such as is standard for broth microdilution AST. For example, for a representative antimicrobial, such as ciprofloxacin, this range may comprise the dilutions: 16 µg/mL, 8 µg/mL, 4 µg/mL, 2 µg/mL, 1 µg/mL, 0.5 µg/mL, 0.25 µg/mL, 0.125 µg/mL, etc. Serial dilution may refer to dilutions by a factor other than 2 (doubling dilution). In certain instances, serial dilutions may be performed by a dilution factor of 5, or a dilution factor of 10 in order to cover the minimum and maximum range desirable within the number of dilutions. However, for the purpose of examples described herein, unless otherwise indicated, a dilution factor is 2.

Half-life: As used herein, the term "half-life" is the time required for a quantity such as nucleic acid or protein concentration or activity to fall to half of its value as measured at the beginning of a time period.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

Master cartridge, patient cartridge, test cartridge: As used herein, master cartridge is the parent cartridge from which daughter "patient" or "sample" cartridges are prepared by dispensing antimicrobial compounds from the master cartridge to the daughter patient cartridges. In some embodiments daughter cartridges have serial dilutions of antimicrobial compounds, whereas the master cartridge comprises the concentrated or lyophilized form of the antimicrobial compounds. As used herein, patient cartridge, daughter cartridge, test cartridge, sample cartridge, or sample test cartridge are used interchangeably, which are distinct from the master cartridge.

Microorganism: As used herein, a microorganism is an organism such as bacteria, a virus, protozoa, algae, fungi or any microbial agent which can cause a disease in a human or an animal subject. A microorganism may also remain latent for indefinite period of time in a subject and may not ever cause a disease.

Minimum inhibitory concentration (MIC): As used herein, the MIC of an antimicrobial refers to the lowest concentration of the antimicrobial at which concentration its antimicrobial activity is detectable.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Reservoir: As used herein the term reservoir is used to represent a housing space for holding a composition, such as a reagent or a sample; for storage, or for preparation of, or for performing an assay. The term may be used interchangeably with "wells" for example, in a cartridge or a multi-well microtiter plate. A reservoir may be a single well structure. The reservoir may also be in any form and shape, including but not limited to round wells, or wells of any shape or size, or elongated channels. A reservoir is meant to hold a fluid or dried/lyophilized powder substance.

Sample: As used herein, the term "sample" refers to a biological sample, a patient sample, or a microorganism-containing sample.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but the subject may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Target microbe: As used herein, a target microbe is a microbe against which the antimicrobial in question is effective as a microbicidal, microbistatic or inhibitory agent to disrupt a certain function of the microbe relating to its infectivity.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

Qualitative Susceptibility Result (QSR): As used herein, the QSR refers to a determination whether or not an antimicrobial has an effect on a microbe, and whether a microbe is susceptible to the antimicrobial and vice versa. For example, the microbe stops growth in presence of the antimicrobial, is an indication that the antimicrobial has an effect on the microbe.

DETAILED DESCRIPTION

The present disclosure provides, among other things, systems and methods for multiplexed AST using single cartridges. In general, the embodiments of this disclosure directed to multiplexed AST utilize cartridges comprising a number of reservoirs that is greater than the number of reservoirs needed for a single AST panel (e.g., two-times, three-times, four-times or more the number of reservoirs needed for AST analysis of a single patient sample). In some cases, the cartridges are configured to provide AST for multiple patient samples on a single cartridge, advantageously reducing the cost per patient sample of AST. Alternatively, or additionally, the cartridges are configured to include multiple AST panels, such as for gram-positive and gram-negative bacteria, for particular categories of antibiotics such as broad- and narrow-spectrum antibiotics, or other specific panels for AST interrogation of specific categories of infectious agents and/or antiboiotics.

In use, a multiplex cartridge according to the embodiments of the disclosure presented above may include two, three or more AST panels, and may be loaded with a single patient sample and processed immediately, or may be loaded with multiple patient samples (e.g., one sample per separate AST panel) and processed such that each AST panel on the cartridge is loaded with a separate patient sample, or such that only one AST panel, or only two AST panels are empty. Once processed, a cartridge may be disposed of, or may be saved for loading unused AST panels with additional patient samples. To facilitate multiple uses, multiplex cartridges may include one or more membranes sealing the wells belonging to each AST panel, to prevent the introduction of fluid into unused AST panels during processing of the cartridge. Alternatively, or additionally, following processing of a panel on a multiplex cartridge, the used wells may be washed, aspirated and/or sealed to prevent their re-use and contamination of other AST panels in the cartridge.

Cartridges according to this disclosure may also be designed to provide quality control for AST systems and methods. As one example, the CLSI recommends daily quality control testing of AST systems using multiple quality control organisms across a series of antimicrobial concentrations which may extend from one-half of the lowest concentration in a predefined QC range for a given antimicrobial and up to twice the maximum concentration in the predefined QC range. Quality control organisms and QC ranges are generally specific for each antimicrobial within an AST panel, though antimicrobials within the same class may have similar or overlapping QC ranges.

Those of skill in the art will appreciate that, for a given AST panel, a plurality of quality control organisms and concentration ranges may need to be examined. QC across these organisms and concentration ranges must be done regularly (e.g., daily or weekly) to ensure the consistency and accuracy of AST results obtained for a given system, and additional testing may be indicated where a quality control organism for a given antimicrobial does not give a result in-range. Those of skill in the art will appreciate that, for smaller AST facilities utilizing current AST systems, the number of quality control tests may approach or even exceed the number of clinical samples examined. AST systems according to certain embodiments of this disclosure utilize cartridges with hundreds of wells, advantageously permitting quality control for multiple quality control organisms and/or breakpoint ranges to be done on a single cartridge. Thus, an advantage of AST systems and methods according to these embodiments is a reduction in the cost and time required for quality control testing, and improving the economic feasibility of AST at lower throughput.

This disclosure also provides master cartridge for creating multiple patient cartridges (i.e., daughter cartridges), wherein the patient cartridges are used for performing one or more multiplex assays for antimicrobial susceptibility. The patient cartridge has greater number of reservoirs having antimicrobials than that of a master cartridge. The patient cartridges or daughter cartridges are dispensable after the test has been performed, whereas, the master cartridge is reusable over a plurality of such test sets, i.e., the master cartridge can be used to prepare a plurality of daughter or patient cartridges. In another aspect, the invention provides a patient cartridge having greater than 150 reservoirs comprising one or more antimicrobials. The invention provides a versatile system to test greater number of antimicrobials and/or greater range of concentrations of the antimicrobials, which could be customized for a patient's needs.

Disadvantages of Existing AST Platforms

A significant shortcoming of current automated phenotypic antibiotic susceptibility testing (AST) platforms is their inability to accommodate newly-approved antibiotics on their menus, resulting in an average of a 5-year delay between new drug approval and presence on automated AST menus. This poses a significant problem for Infectious Disease (ID) patient care because new antibiotics are often more effective and less toxic than generic alternatives and ID doctors cannot confidently prescribe targeted antibiotic therapies without AST results.

Thus, new, highly-effective antibiotics are often underutilized, resulting in increases in mortality and hospital costs, the latter primarily due to increased lengths-of-stay. This also harms Antibiotic Stewardship Program goals, which aim to deliver the most appropriate antibiotic therapy to each patient as quickly as possible. Furthermore, this delay decreases incentives to pharmaceutical companies to develop new antibiotics, a grave international concern given the current antibiotic resistance epidemic.

Phenotypic AST provides the key actionable information to physicians to determine the proper antibiotic therapy by determining the ability of each of a panel of antibiotics to inhibit bacterial growth. This is most commonly determined by broth microdilution (BMD), a method that determines minimum inhibitory concentrations (MICs) for each of a panel of antibiotics for a patient sample. In order to determine an accurate MIC for a given antibiotic, a range of concentrations must be tested. Thus, AST "panels" comprise multiple antibiotics, each tested at a range of concentrations, with each "well" having an antibiotic at a given concentration.

There are three fully-automated phenotypic AST platforms that dominate the clinical laboratory market, the bioMerieux Vitek2®, the Danaher MicroScan®, and the Becton-Dickinson Phoenix®, and one new rapid-AST entrant, the Accelerate Diagnostics Pheno®. Each of these systems performs phenotypic AST determinations by measuring growth of all wells in their panels repeatedly, such as every 15-30 minutes. Results are then reported when the systems' algorithms determine that sufficient delineation between growth and inhibition is available for each antibiotic to make an accurate MIC call.

Although existing AST platforms can provide accurate results, their reliance on repeated measurements places a significant engineering limitation on the number of antibiotics that can be tested in parallel. Thus, these platforms are limited to menus of less than 20 antibiotics (1-14 for the Pheno®, depending on the organism). This limited space provides clinical lab customers with very limited choice of antibiotics to include on their panels: since new antibiotics often cost more than 10 times per dose compared to generics, customers often are forced to forego these in lieu of the more cost-effective options.

In contrast, the Centers for Laboratory Standards Institute (CLSI) BMD reference method, the "gold standard" phenotypic AST method, performs a single, optical read after an incubation of 16-20 hours. This method thus trades off time for simplicity, with only a single, "endpoint" read necessary. In some instances, the method relies on visual (by-eye) interpretation of results. The current provisions allow limited antimicrobial panels occupying 96-well plates.

By emulating the endpoint assay paradigm of the CLSI reference method, the present method enables greater than 150 reservoirs or wells to be multiplexed by removing the engineering pressure to reduce the number of wells per panel. In some embodiments, the present method enables greater than 200 wells for multiplex assays. As described in U.S. Pat. No. 9,834,808, the assay provides accurate AST data after only 3.5-hour incubations. In order to accommodate slow-growing strains, such as vancomycin-intermediate *Staphylococcus aureus* (VISA), the method measures<5 wells per panel to ensure that a "sufficient growth" threshold has been reached in order to begin assay processing. In particular, this allows standard microplate formats of 384 or 1536 wells to be used, and it further enables parallel processing of panels with any number of wells greater than 200.

Further, this method allows for a reduction in cost for quality control. The described method decreases the burden on the user because it decreases the number of panels that must be dedicated to QC. Here, 2, 3, 4, 5, 6, 7, or 8 QC organisms may be run in parallel on a single panel without any changes in the panel antimicrobial concentrations for those used for sample testing. Through such multiplexing of QC organisms, fewer panels need be dedicated to QC. This may be advantageous for laboratories and small laboratories in particular because of the FDA's requirement that new AST platforms perform on-scale QC for all drugs, 6 different QC strains may need to be processed to QC a comprehensive Gram positive AST panel and 5 different QC strains may need to be processed to QC a comprehensive Gram negative AST panel (Table 1). Thus, for a laboratory that runs 5-10 samples per day, dedicating 11 panels per week to QC may increase costs by >15%. Therefore, with the multiplex QC methods described herein, the cost of the consumables for running a standard patient sample may be lower.

TABLE 1

Values for the QC of a comprehensive Gram positive AST panel and the QC of a comprehensive Gram negative AST panel.

| QC Strain | Drug or Screen | SeLux Panel Dilutions for Clinical Samples (μg/mL) | SeLux Panel Dilutions for QC Testing (μg/mL) | CLSI-Defined QC Range (μg/mL) |
|---|---|---|---|---|
| | Gram Negative Drug or Screen | | | |
| E. coli 25922 | Cefoxitin | 1-64 | 1-64 | 2-8 |
| | Eravacycline | 0.016-2 | 0.016-2 | 0.03-0.12 |
| | Cefuroxime | 0.5-64 | 0.5-64 | 2-8 |
| | Ampicillin | 0.25-64 | 0.25-64 | 2-8 |
| | Aztreonam | 0.03-64 | 0.03-64 | 0.06-0.25 |
| | Tetracycline | 0.25-32 | 0.25-32 | 0.5-2 |
| | Cefazolin | 0.12-64 | 0.12-64 | 1-4 |
| | Trimethoprim-Sulfamethoxazole | 0.12-16 | 0.12-16 | ≤0.5/9.5 |
| | ESBL Test (Cefotaxime-Clavulanic Acid and Cefotaxime; Ceftazidime-Clavulanic Acid and Ceftazidime) | Negative | Negative | ≤2 dilutions between drug and drug-inhibitor: CTX-CLV 0.25/4-16/4; CTX 0.25-64; CAZ-CLV 0.25/4-32/4; CAZ 0.25-128 |
| E. faecalis 29212 | Minocycline | 0.25-32 | 0.5-32 | 1-4 |
| | Gentamicin | 0.06-32 | 0.5-32 | 4-16 |
| | Tobramycin | 0.12-64 | 1-64 | 8-32 |
| | Levofloxacin | 0.06-16 | 0.06-4 | 0.25-2 |
| | Meropenem | 0.12-64 | 0.5-32 | 2-8 |
| | Doxycycline | 0.25-32 | 0.5-32 | 2-8 |

TABLE 1-continued

Values for the QC of a comprehensive Gram positive AST panel and the QC of a comprehensive Gram negative AST panel.

| QC Strain | | SeLux Panel Dilutions for Clinical Samples (μg/mL) | SeLux Panel Dilutions for QC Testing (μg/mL) | CLSI-Defined QC Range (μg/mL) |
|---|---|---|---|---|
| K. pneumoniae 700603 | Amoxicillin-Clavulanic Acid | 0.5/0.25-64/32 | 0.5/0.25-64/32 | 4/2-16/8 |
| | Amoxicillin (alone)-QC to ensure plasmid is retained | 128 | >128 | >128 |
| | ESBL Test (Cefotaxime-Clavulanic Acid and Cefotaxime; Ceftazidime-Clavulanic Acid and Ceftazidime) | Positive | Positive | ≥3 dilutions between drug and drug-inhibitor: CTX-CLV 0.25/4-16/4; CTX 0.25-64; CAZ-CLV 0.25/4-32/4; CAZ 0.25-128 |
| | Imipenem | 0.016-32 | 0.016-32 | 0.03-0.25 |
| | Ceftolozane-Tazobactam | 0.25/4-64/4 | 0.25/4-64/4 | 0.5/4-2/4 |
| | Ampicillin-Sulbactam | 0.5/0.25-64/32 | 0.5/0.25-64/32 | 8/4-32/16 |
| | Ampicillin (alone)-QC to ensure plasmid is retained | 0.25-128 | 64 | >128 |
| | Ceftazidime-Avibactam | 0.12/4-32/4 | 0.12/4-32/4 | 0.25/4-2/4 |
| | Ceftazidime (alone)-QC to ensure plasmid is retained | 0.25-128 | 16-64 | 16-64 |
| | Piperacillin-Tazobactam | 2/4-256/4 | 2/4-256/4 | 8/4-32/4 |
| | Aztreonam-Avibactam [will be tested but not submitted for 510(k)] | 0.03/4-64/4 | 0.03/4-64/4 | 0.06/4-0.5/4 |
| | Aztreonam (alone)-QC to ensure plasmid is retained | 0.03-64 | 8-64 | 8-64 |
| S. aureus 29213 | Cefpodoxime | 0.25-16 | 0.25-16 | 1-8 |
| | Moxifloxacin | 0.008-16 | 0.008-16 | 0.016-0.12 |
| | Cefepime | 0.25-64 | 0.25-64 | 1-4 |
| | Cefotaxime | 0.25-64 | 2-64 | 1-4 |
| | Nitrofurantoin | 4-256 | 4-256 | 8-12 |
| | Ceftriaxone | 0.25-16 | 0.25-16 | 1-8 |
| | Ciprofloxacin | 0.03-8 | 0.03-8 | 0.12-0.5 |
| | Amikacin | 0.12-128 | 0.12-128 | 1-4 |
| | Ceftazidime | 0.25-128 | 0.25-128 | 4-16 |
| | Ertapenem | 0.03-8 | 0.03-8 | 0.06-0.25 |
| | Ceftaroline | 0.06-8 | 0.06-8 | 0.12-0.5 |
| K. pneumoniae BAA-2814 | QC organism test to ensure plasmid is retained-imipenem | 0.5-32 | ≥16 | 16-64 |
| | Meropenem-Vaborbactam | 0.06/8-64/8 | 0.06/8-16/8 | 0.12/8-0.5/8 |
| | Imipenem-Relebactam [will be tested but not submitted for 510(k)] Gram Positive Drug or Screen | 0.03/4-64/4 | 0.03/4-64/4 | 0.06/4-0.25/4 |
| S. aureus 29213 | Trimethoprim | 0.25-32 | 0.25-32 | 1-4 |
| | Erythromycin-Induced Clindamycin Resistance | Negative | Negative | Negative (No growth @ 0.5/4) |
| | Clindamycin | 0.03-8 | 0.03-8 | 0.06-0.25 |
| | Vancomycin | 0.12-64 | 0.12-16 | 0.5-2 |
| | Ciprofloxacin | 0.03-8 | 0.03-4 | 0.12-0.5 |
| | Azithromycin (Selux mistake-sorry) | 0.06-32 | 0.06-8 | 0.5-2 |
| | Linezolid | 0.25-16 | 0.25-16 | 1-4 |
| | Penicillin | 0.03-32 | 0.03-8 | 0.25-2 |
| | Ceftaroline | 0.06-16 | 0.06-8 | 0.12-0.5 |
| | Nitrofurantoin | 4-256 | 4-256 | 8-32 |
| | Oxacillin | 0.03-16 | 0.03-2 | 0.12-0.5 |

TABLE 1-continued

Values for the QC of a comprehensive Gram positive AST panel and the QC of a comprehensive Gram negative AST panel.

| QC Strain | | SeLux Panel Dilutions for Clinical Samples (µg/mL) | SeLux Panel Dilutions for QC Testing (µg/mL) | CLSI-Defined QC Range (µg/mL) |
|---|---|---|---|---|
| | Cefoxitin Screen | Negative | Negative | Negative (No growth @ 4) |
| | Trimethoprim-Sulfamethoxazole | 0.12-16 | 0.12-16 | ≤0.5/9.5 |
| | Mupirocin High Level Screen | Negative | Negative | Negative (No growth @ 256) |
| E. faecalis 29212 | Eravacycline | 0.002-0.25 | 0.002-0.25 | 0.016-0.06 |
| | Daptomycin | 0.5-16 | 0.5-16 | 1-4 |
| | Minocycline | 0.12-32 | 0.12-32 | 1-4 |
| | Tetracycline | 0.25-64 | 0.25-64 | 8-32 |
| | Doxycycline | 0.06-32 | 0.06-32 | 2-8 |
| | Rifampin | 0.25-8 | 0.25-8 | 0.5-4 |
| | Gentamicin | 0.12-32 | 0.12-32 | 4-16 |
| | Moxifloxacin | 0.008-8 | 0.25-2 | 0.06-0.5 |
| | Levofloxacin | 4-16 | 4-16 | 0.25-2 |
| | Ampicillin | 8-64 | 8-64 | 0.5-2 |
| | Erythromycin | 0.25-16 | 0.25-16 | 1-4 |
| | Delafloxacin | 0.008-4 | 0.008-1 | 0.016-0.12 |
| | Streptomycin High Level Screen | Negative | Negative | Negative (No growth @ 100 48 hrs if susceptible) |
| | Gentamicin High Level Screen | Negative | Negative | Negative (No growth @ 500 24 hrs) |
| S. aureus BA-977 | Erythromycin-Induced Clindamycin Resistance | Positive | Positive | Positive (Growth @ 0.5/4) |
| S. aureus 43300 | Cefoxitin Screen | Positive | Positive | Positive (Growth @ 4) |
| S. aureus BAA-1708 | Mupirocin High Level Screen | Positive | Positive | Positive (Growth @ 256) |
| E. faecalis 51299 | Streptomycin High Level Screen | Positive | Positive | Positive (Growth @ 100) |
| | Gentamicin High Level Screen | Positive | Positive | Positive (Growth @ 500) |

Traditional automated AST systems are designed to process QC samples similarly to clinical samples, with one panel dedicated to each sample. This is mandated by the design of the Vitek®2 and Phoenix™ consumable panels (cards) and the MicroScan™ inoculator (Renok). The Vitek and Phoenix panels utilize a single inlet to distribute sample to all panel reservoirs and the MicroScan inoculator draws 96 aliquots of the same sample from a single dilution tray. Thus, each QC organism run on these systems must have a dedicated panel.

It is further important to note that the number of required QC organisms may be higher for new systems because of 1) the FDA's recent requirement for on-scale QC for commercial panels and 2) the presence of new antibiotics that require new QC organisms, such as beta-lactam/beta-lactamase inhibitor combination therapeutics. Thus, panels enabling multiplex QC and methods for processing these are of particular importance currently.

In order to meet the FDA requirement for on-scale QC, new systems such as the Accelerate Diagnostics Pheno™ have developed complex cartridges (panels) that alter the actual concentration(s) of antimicrobials tested depending on a user selection of a clinical or QC sample. Despite the ingenuity of this approach, the cost of the resulting cartridges capable of such "dynamic dilutions" may be significantly higher than those of "static concentration" panels, such as those described herein. The panels and QC methods described herein are designed such that each reservoir comprising an antimicrobial contains the same amount of drug whether a clinical or QC (or test) sample is processed. The preferred method is to test the same concentration of antimicrobial for clinical and QC samples, though it should be noted that it would be feasible for a QC run to test, for example, half the clinical concentration by adding double the volume of solution to the reservoir.

Multiplex Assays

By running large numbers of multiplex assays in parallel per patient sample, the present platform is able to address three specific user requirements: first, that large numbers of antibiotics, including recently-approved drugs, be available on standard panels; second, that "full" dilution series be utilized; and third, that accuracy is increased by performing replicate tests around breakpoint regions.

In one embodiment, each patient sample can be tested with greater than or equal to 3 antimicrobials in parallel. In one embodiment, each patient sample can be tested with greater than or equal to 4, 5, 6, 7, 8, 9, 10, 11, 12, 13, 14, 15, 16, 17, 18, 19, 20, 21, 22, 23, 24, 25, 26, 27, 28, 29 or greater than or equal to 30 antimicrobials in parallel. For Gram-negative organisms, in particular, each patient sample can be tested with greater than or equal to 35 antibiotics in parallel. In addition to testing all standard generic antibiotics of all classes, these may include newly-approved and yet-to-be-approved antibiotics including, but not limited to: Avycaz, Vabomer, Zerbaxa, Tedizolid, Tigecycline, Doripenem, Delafloxacin, Oritavancin, Telavancin, Dalbavancin, Eravacycline, Cefiderocol, Omadacycline, Plazomicin, Iclaprim, Lefamulin, Solithera, Primaxin, SPR-994, and MK-7655.

The large number of wells that can be run in parallel further enables large dilution ranges to be tested. As known to those skilled in the art, the CLSI standard is to run serial (or two-fold) dilution ranges of each antibiotic to accurately determine the MIC. The ranges include the "breakpoint" range, the MIC value(s) at which the FDA and CLSI determine that the drug will be clinical effective ("susceptible, S") or ineffective ("resistant, R"). For example, a drug such as oxacillin with *Staphylococcus aureus*, an MIC of 2 µg/mL or lower is interpreted to mean the strain is susceptible and the drug should be used, whereas an MIC of 4 µg/mL and higher means the organism is resistant and would be clinically ineffective. Since there are no dilutions between these test wells, most drugs, such as Ertapenem with *Escherichia coli*, have an additional, "intermediate," breakpoint to provide an intermediate, buffer region, where clinical use is generally dependent upon breakpoints to other drugs. An exemplary breakpoint table for commonly used antimicrobials known to be effective against Enterobacteriaceae and *P. aeruginosa* are provided in Table 2. Additional information may be accessed from the following references: Clinical and Laboratory Standards Institute (CLSI) publication "M100—Performance Standards for Antimicrobial Susceptibility testing," the FDA website at https://www.fda.gov/Drugs/DevelopmentApprovalProcess/DevelopmentResources/ucm575163.htm, and the EUCAST website http://www.eucast.org/clinical_breakpoints.

TABLE 2

FDA Breakpoints for determining susceptibility or resistance to antimicrobials for two exemplary bacteria.
FDA Breakpoints (≤S |I| ≥R)

| Drug | Enterobacteriaceae | | | P. aeruginosa | | |
|---|---|---|---|---|---|---|
| Amikacin | 16 | 32 | 64 | 16 | 32 | 64 |
| Amoxicillin-Clavulanic Acid | 8/4 | 16/8 | 32/16 | | | |
| Ampicillin | 8 | 16 | 32 | | | |
| Ampicillin-Sulbactam | 8/4 | 16/8 | 32/16 | | | |
| Azithromycin | | | | | | |
| Aztreonam | 4 | 8 | 16 | 8 | 16 | 32 |
| Cefazolin | 1 | 2 | 4 | | | |
| Cefepime | 2 | 4-8 | 16 | 8 | | 16 |
| Cefotaxime | 1 | 2 | 4 | | | |
| Cefoxitin | 4 | 8 | 16 | | | |
| Cefpodoxime | 2 | 4 | 8 | | | |
| Ceftaroline | 0.5 | 1 | 2 | | | |
| Ceftazidime | 4 | 8 | 16 | 8 | | 16 |
| Ceftazidime-Avibactam | 8/4 | | 16/4 | 8/4 | | 16/4 |
| Ceftolozane-Tazobactam | 2/4 | 4/4 | 8/4 | 4/4 | 8/4 | 16/4 |
| Ceftriaxone | 1 | 2 | 4 | | | |
| Cefuroxime | 8 | | 16 | | | |
| Ciprofloxacin | 1 | 2 | 4 | 1 | 2 | 4 |
| Clindamycin | | | | | | |
| Colistin | | | | ~2 | ~4 | ~8 |
| Dalbavancin | | | | | | |
| Daptomycin | | | | | | |
| Delafloxacin | 0.25 | 0.5 | 1 | 0.5 | 1 | 2 |
| Doripenem | | | | | 2 | |
| Doxycycline | | | | | | |
| Ertapenem | | | | | | |
| Erythromycin | | | | | | |
| Gentamicin | 4 | 8 | 16 | 4 | 8 | 16 |
| Imipenem | 1 | 2 | 4 | 2 | 4 | 8 |
| Levofloxacin | 2 | 4 | 8 | 2 | 4 | 8 |
| Linezolid | | | | | | |
| Meropenem | 1 | 2 | 4 | 2 | 4 | 8 |
| Minocycline | 4 | 8 | 16 | | | |
| Moxifloxacin | 2 | 4 | 8 | | | |

TABLE 2-continued

FDA Breakpoints for determining susceptibility or resistance to antimicrobials for two exemplary bacteria.
FDA Breakpoints (≤S |I| ≥R)

| Drug | Enterobacteriaceae | | | P. aeruginosa | | |
|---|---|---|---|---|---|---|
| Nitrofurantoin | 32 | 64 | 128 | | | |
| Oritavancin | | | | | | |
| Oxacillin | | | | | | |
| Penicillin | | | | | | |
| Piperacillin-Tazobactam | 16 | 32-64 | 128 | 16 | 32-64 | 128 |
| Quinupristin-Dalfopristin | | | | | | |
| Rifampin | | | | | | |
| Tedizolid | | | | | | |
| Tetracycline | 4 | 8 | 16 | | | |
| Tigecycline | 2 | 4 | 8 | | | |
| Tobramycin | 4 | 8 | 16 | | | |
| Trimethoprim-Sulfamethoxazole | 2/38 | | 4/76 | | | |
| Vabobactam-Meropenem | 4/8 | 8/8 | 16/8 | | | |
| Vancomycin | | | | | | |

With the evolution of microbes and emergence of newer antibiotic resistant varieties of microbes, the standard preset of antimicrobials for AST fall short to meet the requirements for addressing and identifying the antimicrobial that would best fit each patient to treat an infection. The invention is based, in part on a surprising discovery that the ranges of antimicrobials beyond clinical dilution ranges can prove to be advantageous. This necessitates increasing the antimicrobial dilution ranges tested to include dilutions beyond the clinical dilution range. In another embodiment, the invention addresses the need for evaluating slow growing microbes in response to certain antimicrobials or certain concentrations of antimicrobials, such that a perceived positive result of an AST is properly validated, and can provide additional insight into ultimate clinical efficacy of the antimicrobial. The versatility offered by the multiplexing platform disclosed here, offers the advantage of testing not only a greater number of antimicrobials but also a greater range of antimicrobial dilutions. The multiplexing platform offers the ability to customize a particular set of tests as per the requirement of the patient, the disease symptoms and any other relevant factors.

Guidelines for selection of antimicrobials for testing and reporting antimicrobial susceptibility can be had from FDA resources, such as the CLSI M100 guide, the FDA website https://www.fda.gov/Drugs/DevelopmentApprovalProcess/DevelopmentResources/ucm575163.htm. Similarly, recommendations for testing conditions, routine quality control recommendations, suggestions for additional agents that should be considered for routine testing and reporting can also be obtained from the CSLI guide cited above.

An expanded number of wells is able to test each dilution concentration in duplicate, in triplicate or in greater number of replicates, or to test intermediate dilution concentrations (such as 3 µg/mL), and/or to extend the dilution ranges per antibiotic. These may provide greater accuracy and/or information into susceptibility and/or resistance.

An additional advantage of patient cartridges with >200 reservoirs or wells is that multiple patient samples can be processed on a single plate for cases known by those skilled in the art to be "simple," such as uncomplicated urinary tract infections. These cases may require parallel testing with smaller number of antibiotics; thus, to conserve cost and time, it may be beneficial to run multiple samples per single cartridge.

In some embodiments, the patient cartridges with >200 reservoirs is used to accommodate multiple samples collected from the same patient, for example body fluid samples such as blood, CSF, serum, pulmonary lavage, saliva or urine. In general, some samples are collected under aseptic conditions such samples are referred to as sterile samples. For some samples, it is not possible to maintain aseptic conditions, such samples are referred to as nonsterile. A patient cartridge of greater than 200 reservoirs allows testing both sterile and nonsterile samples in the same cartridge, given the possibility of avoiding cross contamination from the two kinds of samples being in adjacent reservoirs.

Master Cartridges

The current standard in automated phenotypic AST is for each patient sample to be tested on a cartridge that is delivered to the laboratory (from the test supplier) with all necessary antibiotics for all dilutions present in the required amounts. This puts the responsibility for accurate antibiotic measurements solely in the factory floor of the manufacturers. The antibiotics are often dried, stabilizing them, such that they may be stored at room temperature or under refrigeration, a significant advantage over frozen (−20° C.) or deep-frozen (−80° C.) storage primarily because of cost. However, it is well known to those skilled in the art that the drying process can have detrimental impacts on antibiotic performance, which may compromise product and result in recalls.

As disclosed herein, the master cartridge is often a single "master" plate which comprises multiple reservoirs, the reservoir comprising antimicrobials in sufficient quantities so as to provide for setting up antimicrobial susceptibility tests (AST) for multiple patient samples and over a range of antimicrobial concentrations. In some embodiments, a single master cartridge enables testing of greater than 25 independent patient samples. The same master cartridge can accommodate a plurality of antimicrobials at quantities or concentrations sufficient for preparing a plurality of antimicrobial susceptibility tests for a plurality of patient samples and multiple reiterations of the same for obtaining confidence in the results. This vastly reduces required storage space, and this may enable antibiotics to be provided to laboratory customers in a frozen or deep-frozen format, which may result in improved batch to catch consistency. Alternatively, the antibiotics may be dried or lyophilized and stored at room temperature or under refrigeration. In some embodiments a master cartridge comprises both individual antimicrobials and antimicrobial combinations. One or more reservoirs in the master cartridge can harbor a combination of more than one antimicrobial compounds.

Accordingly a master cartridge comprises a plurality of reservoirs. In some embodiments the master cartridge comprises 384 or more reservoirs. This allows for introduction of a sufficient number of antimicrobials, including recently approved ones, which is not feasible with 96-reservoir cartridges. It further allows for customization of the antimicrobial panel on each patient plate.

In some embodiments, the master cartridge is designed such that it can undergo multiple freeze thaw cycles without any damage or loss of activity of the antimicrobial compounds. In some embodiments the master cartridge is capable of withstanding extreme temperatures such below −80° C. and can be maintained without undergoing structural damage, such as cracking or warping over a wide range of temperatures.

In some embodiments, the master cartridge comprises one or more encasements or seals. An outer seal or encasement may be present which serves to isolate the cartridge from contamination prior to use. This is useful for transportation and storage of the cartridge. In some embodiments the reservoirs are sealed by another encasement. In some embodiments each reservoir is individually sealed. In some embodiments, each reservoir is sealed by an airtight covering. Additionally each reservoir seal may be individually operable. In some embodiments the encasement is a pouch, which is sealed. In some embodiments the sealed pouch comprises a master cartridge. A master cartridge comprising antimicrobials in solid form is sealed in presence of a desiccant inside the pouch, to keep it dehydrated. Therefore, a pouch comprising a master cartridge and a desiccant is used to seal a master cartridge comprising antimicrobials in solid state. Further, a master cartridge comprising antimicrobials in a solvated form can sealed with an adhesive sealer and/or stored or shipped inside the pouch.

In some embodiments the master cartridge is transparent. In some embodiments the master cartridge is light protected. In some embodiments the master cartridge allows light to penetrate through the base of the reservoirs.

In some embodiments, the master cartridge comprises matrix tubes.

In some embodiments, a master cartridge provides sufficient antimicrobials to prepare 50-100, 100-250, 250-500, 600-750 or 750-1,000 patient cartridges or microtiter plates.

In some embodiments, the master cartridge comprises at least 10 fold higher amount of each antimicrobial required for the highest desired testing concentration in a patient cartridge. In some embodiments, the master cartridge comprises at least 20 fold higher amount of each antimicrobial required for the highest desired testing concentration in a patient cartridge. In some embodiments, the master cartridge comprises at least 30, at least 40, at least 50, at least 60, at least 70, at least 80, at least 90, at least 100 fold higher amount of each antimicrobial required for the highest desired testing concentration in a patient cartridge. In some embodiments, the master cartridge comprises at least 200 fold higher amount of each antimicrobial required for the highest desired testing concentration in a patient cartridge. In some embodiments, the master cartridge comprises at least 500 fold higher amount of each antimicrobial required for the highest desired testing concentration in a patient cartridge. In some embodiments, the master cartridge comprises at least 1,000 fold higher amount of each antimicrobial required for the highest desired testing concentration in a patient cartridge. In some embodiments, the master cartridge comprises at least 10,000 fold higher amount of each antimicrobial required for the highest desired testing concentration in a patient cartridge. In some embodiments the master cartridge comprises as high as $10^6$ fold higher the amount of each antimicrobial required for the highest desired testing concentration in a patient cartridge. In some embodiments, the antimicrobials in the master cartridge are in lyophilized or otherwise dried solid form. In such embodiments, it is necessary to solubilize or solvate the solid form into a high concentration stock solution for each antimicrobial to aliquot a fraction of the solution into a patient cartridge or an auxiliary reservoir or dilution reservoir. A number of serial dilutions can be generated from the master cartridge for a patient cartridge.

In some embodiments the antimicrobials are in solution in a master cartridge. The total volume of liquid is kept as low as possible, and the concentration of the antimicrobials is kept high. In some embodiments, the volume per reservoir containing an antimicrobial is 1 ml. In some embodiments, the volume per reservoir containing an antimicrobial is 0.5 ml. In some embodiments, the volume per reservoir containing an antimicrobial compound is 0.1 ml.

In some embodiments the antimicrobials are solvated in the master cartridge in an aqueous solvent. In some embodiments the antimicrobials are solvated in the master cartridge in an organic solvent. Examples or organic solvents include but are not limited to dimethyl sulfoxide (DMSO), dimethyl formamide (DMF), ethanol, methanol, acetone, and N-methyl-2-pyrrolidone. In some embodiments a buffered aqueous solvent is used, for example, phosphate buffered saline (PBS).

In some embodiments, the antimicrobial is first solvated in a solvent or a solution having a pH greater than 8. In some embodiments, some antimicrobials are solvated using a solvent having a pH greater than 8.1, or 8.2, or 8.3, or 8.4 or 8.5 or 8.6 or 8.7 or 8.8, or 8.9, or greater than pH 9.0. In some embodiments an antimicrobial is first solvated in a solvent or a solution having a pH less than 7. In some embodiments some antimicrobials are solvated using a solvent having a pH less than 7, or less than 6 or less than 5 or less than 4 or less than 3. In some embodiments the antimicrobial is first solvated in an organic solvent. In some embodiments, the antimicrobial is first solvated using a first volume of a suitable solvent, and the remaining volume is made up with an aqueous solvent, or with water in order to achieve the desired concentration.

This approach requires a liquid handler to aliquot the antibiotics from the master cartridge or plate to "patient" or "daughter" cartridge or plates. The antibiotics may thus be present in the master plate at concentrations that are a multiple of the concentrations required in patient cartridges or plates. For example, for a daughter dilution series of 16 µg/mL, 8 µg/mL, 4 µg/mL, 2 µg/mL, 1 µg/mL, and 0.5 µg/mL the master plate may comprise concentrations of 320 µg/mL, 160 µg/mL, 80 µg/mL, 40 µg/mL, 20 µg/mL, and 10 µg/mL, such that each well is diluted 20-fold in concentration in transfer from master-to-daughter patient cartridges.

The master plate may also be designed to require fewer dilutions, conserving wells. This may be advantageous for utilizing 96-well master plates for use with 384- or 1536-well daughter plates, which may have advantages for high-volume plate filling. For example, for a daughter dilution series of 16 µg/mL, 8 µg/mL, 4 µg/mL, 2 µg/mL, 1 µg/mL, and 0.5 µg/mL the master plate may only comprise concentrations of 320 µg/mL, 40 µg/mL, and 10 µg/mL. In this case, the daughter plates would be filled with two different dilutions for each master concentration, 20-fold and 40-fold.

Additionally, greater numbers of dilutions in transfers may be performed. In the extreme case, each antibiotic may only comprise a single concentration, which is aliquoted into the appropriate daughter plate dilution range by the liquid handler.

In some embodiments, a master cartridge comprises three 96 well plates, one comprising antimicrobials for gram negative bacteria only, one comprising antimicrobials for gram positive bacteria only and one comprising the broad spectrum antimicrobials that work on both gram positive and gram negative bacteria (the broad spectrum plate). In some embodiments, master cartridge may comprise all antimicrobials laid out on the single master cartridge plate.

The transfer of antimicrobials from master-to-patient cartridge is accomplished by a liquid handler. Exemplary platforms include the Hamilton *Nexus* and Starlit and the Dynamic Devices Lynx. Other off-the-shelf or custom platforms comprising similar robotics and liquid handlers may also be utilized. These platforms may aliquot antibiotics, broth, and patient sample, therefore allowing daughter cartridges to "arrive" to the machine empty, greatly increasing storage and handling ease for laboratory customers. The liquid handlers may further enable antibiotic customization, such that only a subset of antibiotics is tested for specific patient samples. Alternatively, antibiotic selection/suppression may be made at the software level of the AST analyzer.

Additional benefits of the master-to-daughter antibiotic transfer approach the ability to accommodate antibiotics that are sparingly (or not at all) soluble in water. Solubilization for these agents may be enhanced through the use of detergents or other liquids or through the use of non-aqueous solvents. These may be present in the master cartridge itself and/or in reagent packs added to the liquid handler that prepares daughter plates.

In some embodiments, master cartridges can be designed such that antimicrobials derived from two or more different master cartridges are comprised on a patient cartridge.

In some embodiments the antimicrobials are lyophilized onto the master cartridge.

In some embodiments the antimicrobials are present in the master cartridge as dry powder.

In some embodiments the antimicrobials are present in a solution in high concentration.

Antimicrobials stored in master cartridge are at least greater than 20-fold concentrated than the minimal inhibitory concentration (MIC) for the antimicrobial for a target microbe. Antimicrobials are present in the master cartridge at a concentration that is at least greater than 30-fold, 40-fold, 50-fold, 60-fold, 70-fold, 80-fold, 100-fold or 200-fold or 500-fold concentration than the minimal inhibitory concentration (MIC) for the antimicrobial for a target microbe. In some embodiments the master cartridge comprises as high as 1000-fold the amount of each antimicrobial required to prepare one patient cartridge.

In some embodiments, each reservoir in a master cartridge contains greater than 1 microgram of the antimicrobial. In some embodiments, each reservoir in a master cartridge contains greater than 1 milligram of the antimicrobial. In some embodiments, each reservoir in a master cartridge contains greater than 10 milligrams of the antimicrobial. In some embodiments, each reservoir in a master cartridge contains greater than or equal to 100 milligrams of the antimicrobial. In some embodiments, each reservoir in a master cartridge contains greater than or equal to 1 gram of the antimicrobial. In some embodiments, each reservoir in a master cartridge contains greater than or equal to 10 grams of the antimicrobial. In some embodiments, each reservoir in a master cartridge contains as much as 100 grams of the antimicrobial. In some embodiments the antimicrobials in the master cartridge are stable through more than one freeze-thaw cycles. The high concentration of the antimicrobials in the master cartridge is such that one or more freeze thaw cycles cannot affect the integrity or functional efficacy of the antimicrobials.

In some embodiments, the master cartridge comprises 384 well microtiter plate.

In some embodiments the master cartridge comprises one or more seals. In some embodiments, an outer seal isolates the cartridge from the surrounding. This may be particularly beneficial for transportation and maintaining sterility. In some embodiments the master cartridge comprises an inner seal covering the one or more reservoirs.

In some embodiments the master cartridge is used to set up a multiplex AST assay for performing a plurality of different assays sharing an incubation period, wherein each assay comprises a microorganism growth assay in the presence of one or more antimicrobials, wherein the plurality of different assays are performed on a patient cartridge comprising one or more reservoirs and one or more antimicrobial compounds, wherein the antimicrobials in the cartridge are transferred to the patient cartridge from a master cartridge that contains each antimicrobial compound present at sufficient mass such that solvation in 0.1 mL of suitable solvent yields an antimicrobial concentration>10-fold higher than the highest desired testing concentration; and determining antimicrobial susceptibility of the one or more microorganisms based on relative microorganism growth.

The master cartridge is not brought in contact with any patient sample, and therefore can be reused to set up multiple rounds of such assays at different times.

Patient Cartridge

In certain cases it may be preferable to have a patient cartridge with antimicrobials dried or frozen solvated at amounts appropriate for direct testing with samples comprising microorganisms derived from patient samples. Existing methods for performing automated AST interrogate reservoirs multiple times throughout the incubation period of the sample under test with antimicrobials comprised in the patient cartridge. This approach produces a growth curve that can be utilized to determine an MIC or growth/no-growth parameter for antimicrobials under test. However, the need for repetitive testing, combined with the throughput requirements of typical hospital clinical microbiology laboratories (for example, up to 170 ASTs per day for a hospital with 1034 beds), limit the number of reservoirs per cartridge.

New approaches for automated AST, such as those described in earlier filings U.S. Pat. No. 9,834,808; pending U.S. application Ser. No. 15/717,569 filed on Sep. 27, 2017, U.S. Provisional Application 62/524,972, filed on Jun. 26, 2017; published PCT Application WO2017185012, filed on Apr. 21, 2017 and pending PCT Application PCT/US17/68306 filed on Dec. 22, 2017; all of which are incorporated by reference herein, may perform AST with fewer reservoir interrogations. In particular, such methods may not require growth curves to report MICs. This advancement may enable patient cartridges with ≥150 reservoirs to be utilized with automated AST platforms, such as those described in our above mentioned Applications and Patent.

The number of reservoirs may be determined by considering the number of antimicrobials to be tested multiplied by the number of desired dilutions. In some embodiments, the required number of dilutions of one antimicrobial is different from that of another. As shown in Table 3 depicting calculations for an exemplary patient cartridge, the required number of inoculation reservoirs can be derived by calculating the sum of the number of dilutions necessary for all antimicrobials, which comprises (a) antimicrobials known to be effective against both gram positive and gram negative bacteria ("Broad Spectrum", Combo) (x), (b) antimicrobials known to be effective against gram positive (y), and (c) antimicrobials known to be effective against gram negative bacteria (z) (=x+y+z). There are 51 different antimicrobials selected to be tested here. At least 128 reservoirs are required for the Broad Spectrum antimicrobials, at least 115 reservoirs for antimicrobials against gram negative and at least 102 reservoirs for antimicrobials against gram positive antimicrobials The exemplary patient cartridge in Table 3 therefore comprises at least 243 reservoirs for gram-negative bacteria and at least 230 reservoirs for gram-positive bacteria. In alternative embodiments all dilutions may be prepared on a single plate for all bacteria, comprising 345 reservoirs.

TABLE 3

Patient cartridge reservoirs for inoculation

| Type | Antibiotic | Abbreviation | Required Min | Required Max | Number Dilutions |
|---|---|---|---|---|---|
| Broad Spectrum | Amikacin | AMK | 0.5 | 128 | 9 |
| Broad Spectrum | Ampicillin | AMP | 0.0625 | 64 | 11 |
| Broad Spectrum | Ciprofloxacin | CIP | 0.03125 | 8 | 9 |
| Broad Spectrum | Ceftriaxone | CRO | 0.25 | 16 | 9 |
| Broad Spectrum | Ceftazidime/Avibactam | CZA | 2/4 | 32/4 | 5 |
| Broad Spectrum | Doxycycline | DOX | 1 | 32 | 6 |
| Broad Spectrum | Cefoxitin | FOX | 1 | 32 | 6 |
| Broad Spectrum | Gentamicin | GEN | 0.25 | 32 | 8 |
| Broad Spectrum | Levofloxacin | LVX | 0.25 | 16 | 7 |
| Broad Spectrum | Minocycline | MNC | 0.5 | 32 | 9 |
| Broad Spectrum | Moxifloxacin | MXF | 0.5 | 16 | 6 |
| Broad Spectrum | Nitrofurantoin | NIT | 4 | 256 | 7 |
| Broad Spectrum | Ampicillin/sulbactam | SAM | 1/0.5 | 64/32 | 7 |
| Broad Spectrum | Trimethoprim/Sulfamethoxazole (1:20) | SXT | 0.5 | 64 | 8 |
| Broad Spectrum | Tetracycline | TET | 0.25 | 32 | 8 |
| Broad Spectrum | Tigecycline | TGC | 0.015625 | 16 | 11 |

TABLE 3-continued

Patient cartridge reservoirs for inoculation

| Type | Antibiotic | Abbreviation | Required Min | Required Max | Number Dilutions |
|---|---|---|---|---|---|
| Broad Spectrum | Tobramycin | TOB | 0.125 | 32 | 9 |
| GramNEG | Amoxicillin/Clavulanic Acid | AMC | 1/0.5 | 64/32 | 7 |
| GramNEG | Aztreonam | ATM | 1 | 64 | 7 |
| GramNEG | Ceftolozane-Tazobactam | C/T | 0.25/4 | 64/4 | 9 |
| GramNEG | Ceftazidime | CAZ | 0.5 | 32 | 7 |
| GramNEG | Ceftazidime/Clavulanate | CAZ/CLV | 0.5/4 | 0.5/4 | 1 |
| GramNEG | Cefuroxime | CFX or CXM | 1 | 64 | 7 |
| GramNEG | Cefazolin | CFZ | 0.25 | 32 | 8 |
| GramNEG | Cefpodoxime | CPD | 0.5 | 16 | 6 |
| GramNEG | Colistin | CST | 0.125 | 8 | 7 |
| GramNEG | Cefotaxime | CTX | 0.25 | 64 | 9 |
| GramNEG | Cefotaxime/Clavulanate | CTX/CLV | 0.5/4 | 0.5/4 | 1 |
| GramNEG | Doripenem | DOR | 0.0625 | 8 | 10 |
| GramNEG | Ertapenem | ERT | 0.03125 | 16 | 10 |
| GramNEG | Cefepime | FEP | 0.25 | 32 | 10 |
| GramNEG | Cefepime/Clavulanate | FEP/CLV | 1/10 | 1/10 | 1 |
| GramNEG | Imipenem | IMP | 0.125 | 32 | 9 |
| GramNEG | Meropenem | MEM | 0.125 | 16 | 8 |
| GramNEG | Piperacillin/Tazobactam | TZP | 4/4 | 256/4 | 7 |
| GramPOS | Azithromycin | AZM | 0.25 | 16 | 7 |
| GramPOS | Clarithromycin | CLR | 0.06 | 16 | |
| GramPOS | Clindamycin | CLI | 0.03125 | 16 | 10 |
| GramPOS | Clindamycin/Erythromycin | CLI/ERY | 0.5/1 | 0.5/4 | 1 |
| GramPOS | Ceftaroline | CPT | 0.03125 | 8 | 9 |
| GramPOS | Daptomycin | DAP | 0.0625 | 8 | 10 |
| GramPOS | Erythromycin | ERY | 0.125 | 16 | 8 |
| GramPOS | Gentamicin HL | GENHL | 500 | 500 | 1 |
| GramPOS | Linezolid | LNZ | 0.25 | 16 | 7 |
| GramPOS | Mupirocin (HL) | MUPHL | 256 | 256 | 1 |
| GramPOS | Oxacillin | OXA | 0.03125 | 8 | 9 |
| GramPOS | Benzylpenicillin (Penicillin G) | PEN | 0.03125 | 16 | 10 |
| GramPOS | Quinupristin/Dalfopristin (30:70) | QNP/DFP | 0.125 | 8 | 7 |
| GramPOS | Rifampin | RIF | 0.25 | 8 | 6 |
| GramPOS | Streptomycin HL | STPHL | 1000 | 1000 | 1 |
| GramPOS | Tedizolid | TDZ | 0.125 | 4 | 6 |
| GramPOS | Vancomycin | VAN | 0.25 | 64 | 9 |

A 384 well cartridge format is described herein, and was shown to yield reproducible and reliable MIC data. Usually a plate having greater than 96 wells is not preferred because of smaller well capacity, and especially evaporation of the solution could affect data outcome when working with a small volume of liquid. Additionally it was observed that there occurs an uneven loss of solution based on the position of a well on the plate. Wells at the periphery undergo greater level of evaporation than the wells toward the center of the well, as shown in the simple test depicted in an exemplary test herein. It was therefore surprising and unexpected, that the AST assay would be successful when performed in a 384 well plate. On the contrary, data from 384 well plate assays were highly reliable.

Antimicrobials

Any antimicrobial can be adapted to the system provided in the disclosure. Examples include but are not limited to Amikacin, Amikacin-fosfomycin, Amoxicillin, Amoxicillin-clavulanate, Ampicillin, Ampicillin-sulbactam, Azithromycin, Azlocillin, Aztreonam, Aztreonam-avibactam, Besifloxacin, Biapenem, Cadazolid, Carbenicillin, Cefaclor, Cefamandole, Cefazolin, Cefdinir, Cefditoren, Cefepime, Cefepime-tazobactam, Cefetamet, Cefixime, Cefmetazole, Cefonicid, Cefoperazone, Cefotaxime, Cefotetan, Cefoxitin, Ceftolozane-tazobactam, Cefpodoxime, Cefprozil, Ceftaroline, Ceftaroline-avibactam, Ceftazidime, Ceftazidime-avibactam, Ceftazidime-avibactam, Ceftibuten, Ceftizoxime, Ceftobiprole, Ceftolozane-tazobactam, Ceftriaxone, Cefuroxime, Cephalothin, Chloramphenicol, Cinoxacin, Ciprofloxacin, Clarithromycin, Clinafloxacin, Clindamycin, Colistin, Dalbavancin, Daptomycin, Delafloxacin, Dirithromycin, Doripenem, Doxycycline, Enoxacin, Eravacycline, Ertapenem, Erythromycin, Faropenem, Fidaxomicin, Finafloxacin, Fleroxacin, Fosfomycin, Fusidic acid, Garenoxacin, Gatifloxacin, Gemifloxacin, Gentamicin, Gepotidacin, Grepafloxacin, Iclaprim, Imipenem, Imipenem-relebactam, Kanamycin, Lefamulin, Levofloxacin, Levonadifloxacin, Linezolid, Linopristin-flopristin, Lomefloxacin, Loracarbef, Mecillinam, Meropenem, Methicillin, Mezlocillin, Minocycline, Moxalactam, Moxifloxacin, Nafcillin, Nalidixic acid, Netilmicin, Nitrofurantoin, Norfloxacin, Ofloxacin, Omadacycline, Oritavancin, Oxacillin, Penicillin, Piperacillin, Piperacillin-tazobactam, Plazomicin, Polymyxin B, Quinupristin-dalfopristin, Razupenem, Rifampin, Solithromycin, Sparfloxacin, Sulfisoxazole, Sulopenem, Tedizolid, Teicoplanin, Televancin, Telithromycin, Tetracycline, Ticarcillin, Ticarcillin-clavulanate, Tigecycline, Tobramycin, Trimethoprim, Trimethoprim-sulfamethoxazole, Trospectomycin, Vancomycin, Aculeacin A, Amphotericin B, Caspofungin, Clotrimazole, Fluconazole, Flucytosine, 5-Fluorocytosine, Griseofulvin, Itraconazole, Ketoconazole, Nystatin, Sordarin, Terbinafine, Voriconazole and theirs salts or hydrates.

In some embodiments the antimicrobials are chemically synthesized molecules. In some embodiments the antimicrobials are chemical compounds. In some embodiments the antimicrobials are biomolecules such as peptides. In some embodiments the antimicrobials are biomolecules such as nucleotides or amino acids. In some embodiments the antimicrobials are biologically molecules. In some embodiments the antimicrobials are antibodies.

The antimicrobials can be stable at room temperature. In some embodiments the antimicrobials are not stable at room temperature in solubilized form. In some embodiments the antimicrobials are susceptible to degradation when stored at a higher temperature, such as room temperature. Several activity assays are available to measure the half-life of an antimicrobial under any conditions over any period of storage. Such methods of assay are well known to one of skill in the art and are not covered in the present disclosure. Creating and storing master cartridges at high antimicrobial concentrations or as dry powder extends the half-life of an antimicrobial. In some embodiments, antimicrobials are stable through multiple freeze-thaw cycles when stored in a master cartridge. In some embodiments the antimicrobials present in dry form, and are solvated in a suitable solvent and/or further diluted. Solvation fluid can be an organic solvent, or an inorganic solvent, acidic or basic in nature. Further dilution is carried out in water. Table 4 provides the suitable solvents for common antimicrobials necessary for AST assays.

TABLE 4

Antimicrobial solvents.

| Drug | Solvent |
|---|---|
| Amikacin | Water |
| Amoxicillin | 3 mL DMSO, 0.01M Phosphate Buffer pH 8.0 at time of fill |
| Ampicillin | 0.1M Phosphate Buffer pH 8.0 |
| Avibactam | Water |
| Avibactam | Water |
| Azithromycin | 95% Ethanol |
| Aztreonam | Water |
| Cefazolin | 0.1M Phosphate Buffer pH 6.0 |
| Cefepime | 5 mL DMSO, 0.01M Phosphate Buffer pH 8.0 at a time to fill |
| Cefotaxime | Water |
| Cefoxitin | Water |
| Cefpodoxime | 0.1% Sodium bicarbonate |
| Ceftaroline | 30% DMSO/70% saline |
| Ceftazidime | Water |
| Ceftazidime | Water |
| Ceftolozane | Water |
| Ceftriaxone | Water |
| Cefuroxime | 0.1M Phosphate Buffer pH 6.0 |
| Ciprofloxacin | 5 mL H2O, add 1 mL 5N NaOH, and 4 mL H2O |
| Clavulanic Acid | 0.1M Phosphate Buffer pH 6.0 |
| Clindamycin | Water |
| Colistin | Water |
| Daptomycin | Water |
| Doxycycline | Water |
| Ertapenem | 0.01M Phosphate Buffer pH 7.2 |
| Erythromycin | 95% Ethanol |
| Gentamicin | Water |
| Imipenem | 0.01M Phosphate Buffer pH 7.2 |
| Levofloxacin | 3 mL H2O, add 1 mL 5N NaOH, and 1 mL H2O |
| Linezolid | 95% Ethanol |
| Meropenem | Water |
| Minocycline | Water |
| Moxifloxacin | Water |
| Nitrofurantoin | DMSO |
| Norfloxacin | 3 mL H2O, add 2 mL 5N NaOH, and 2 mL H2O |
| Oxacillin | Water |
| Penicillin | Water |
| Piperacillin | Water |

TABLE 4-continued

Antimicrobial solvents.

| Drug | Solvent |
|---|---|
| Quinupristin/Dalfopristin | Water |
| Rifampin | Methanol |
| Sulbactam | Water |
| Sulfamethoxazole | Acetone |
| Tazobactam | Water |
| Tedizolid | DMSO |
| Teicoplanin | Water |
| Tetracycline | 3 mL MeOH + 2 mL water. 5N NaOH after diluting |
| Tigecycline | Water |
| Tobramycin | Water |
| Trimethoprim | Water |
| Vancomycin | Water |

An assay setup comprises preparation of patient (target) cartridge by dispensing antimicrobials were from the master cartridge or intermediate serial dilution cartridges into one or more 384 reservoir patient cartridge, each antimicrobial in about 7 serial dilutions in triplicate, and covering the dynamic range of each antimicrobial that is known to be effective and therefore should be reported. The dilution range included the expected minimum inhibitory concentration (MIC) for each antimicrobial. But most importantly, dilution ranges, that is, antimicrobial concentrations beyond the range known to be effective are included in the patient cartridge as per the present invention.

The remaining reservoirs of the 384 well patient cartridge are utilized for setting up test controls: a no-antimicrobial control (negative control) was included for each antimicrobial compound; and a positive control was included for each antimicrobial set, where a microorganism that is not susceptible to the antimicrobial was added to the well. Each control set was also dispensed at least in duplicate per 384 well cartridge. Additional test controls may be included as deemed necessary by one of skill in the art. Equal amount of a patient sample was dispensed to each of the wells in the cartridge, except in the wells designated for no-sample control, if included. The patient cartridge was ready for determination of susceptibility of microbes from the patient sample to the twelve antimicrobials at the range of concentrations applied, simultaneously. Multiple such plates can be set up in parallel for testing samples from multiple patients, each patient sample per plate. An AST assay was performed on the prepared patient cartridges.

In general, AST assays are performed using 24 well-96 well plates. As disclosed herein, in some embodiments the AST assay is performed in 384 well plates. Applicants show that high quality AST results could be obtained using a 384 well plate assay. Since the volume of each reservoir in a 384 well plate is considerably smaller than the 96 well plate, reagents are proportionately scaled down for the assay, thereby posing considerable uncertainty of the assay and data reliability. For example, evaporation could affect the concentrations of the solutions within, and the rate of bacterial growth or a chemical reaction. Surprisingly, it was found that the assay method used as per the invention led to successful AST assays and reliable results when performed on a 384 well plate.

Diagnostic or Therapeutic Applications

The cartridges and methods described herein can be effective in diagnosing the nature of a microbial population in the biological sample from a subject. The subject can be a human patient. The subject can also be a non-human animal. The biological sample is obtained from the patient for analysis. The biological sample can be selected from a group consisting of blood, plasma, blood component, sputum, urine, an exudate, nasal swab, vaginal swab, throat swab, sweat, eye discharge or tissue homogenate. Information regarding susceptibility to one or more antimicrobial in qualitative and quantitative assessment is obtained as a result of the product and methods described herein.

The present invention may be used to treat various diseases, disorders and conditions. Determination of an antimicrobial which is effective against one or more microbe in a patient during a short period of investigation as well as obtaining an MIC value positively impact treatment decisions by a practitioner. The present invention facilitates such outcome in a number of ways. For example, availability of master cartridge could overcome shipping distance barriers, weight restrictions, temperature and stability concerns, and therefore makes an antimicrobial screening endeavor possible at a location of a microbial infection outbreak. Moreover, since multiple "daughter" cartridges can be generated from a master cartridge, the ability for large scale screening of both qualitative and quantitative nature using the patient sample directly, or with multiple patient samples simultaneously, obviates the necessity to identify the microorganism before starting an effective therapeutic approach without delay to the patient(s). The approach aids determination of effective therapeutic dose of the antimicrobial of choice. Thirdly, the batch to batch variability is reduced using the master cartridge approach, allowing reproducibility of diagnostic and therapeutic decisions.

In some embodiments, master cartridges are prepared for downstream use in analyzing antimicrobials for certain indications, where a practitioner of the art would expect a certain group of antimicrobials to work. A close comparison of such antimicrobials for selection of the most effective antimicrobial for a given indication would require such antimicrobials to be selective present in a single set. Therefore, by carefully selecting antimicrobials that can be included in a master cartridge, several platform antimicrobial AST arrays can be custom-generated as per necessity and demand in the field.

EXAMPLES

While certain articles, compositions and methods have been described with specificity in accordance with certain embodiments, the following examples serve only to illustrate embodiments of the invention and are not intended to limit the same.

Example 1: Freezer Space Usage in Multiplex Assays Using Master Cartridge

This example depicts an estimate of freezer space saved by shipping and storing the AST assay cartridges in a master cartridge format. A master cartridge as per the invention is shipped and stored in freezer as an alternative of the commonly prevalent procedure of shipping and storing test cartridges (i.e., patient cartridges) until use. A master cartridge comprising antimicrobials in high concentration and sufficient mass to In this example, a master cartridge is a stack of three 96 well plates, which require a space of 513 $cm^3$. The master plate stack requires a footprint of 128 mm×85 mm×47 mm. A master plate can generate a daughter set of patient cartridge of fifty plates, each plate having 384 reservoirs (wells). Therefore the master cartridge is equivalent to fifty 384 disposable well plates, which have a stacked calculated footprint of 8810 $cm^3$ (FIG. 1). The daughter plates are generated from the master cartridge on the day of the assay and therefore are dispensed once the assay is complete. Therefore, using a master cartridge reduces a shipping and freezer storage space by 17 fold.

Example 2. Layout of Antimicrobials on a Master Cartridge

This example depicts a layout of antimicrobials on a master cartridge. In this example, three 96 well plates was used for master cartridge as shown in FIG. 2. Each master cartridge contains three types of antimicrobials: (1) ones that are "broad spectrum" antimicrobials, effective against both (the term "combo" is often used interchangeably herein with broad spectrum to designate this category) (2) ones that are known to be effective against gram negative bacteria, and (3) ones that are known to be effective against gram positive bacteria. Accordingly as shown in FIG. 2, plate comprising the Broad Spectrum antimicrobials, a plate comprising the gram negative antimicrobials and a plate comprising the gram positive antimicrobials are laid out. The master cartridge comprises high concentration of each antimicrobial (at least greater than five-fold of the highest concentration to be tested). For example, highest concentration of ampicillin recommended for testing in is 64 µg/ml. The highest concentration of ampicillin present in the master plate is 400 µg/ml. Additionally, the master cartridge also comprises sufficient mass of each antimicrobial adapted to prepare multiple patient cartridge from a single master cartridge.

Example 3. Preparation of Patient Cartridge

In this example a step by step set up of patient cartridge from master cartridge for performing an automated AST assay is provided.

Figure 3:
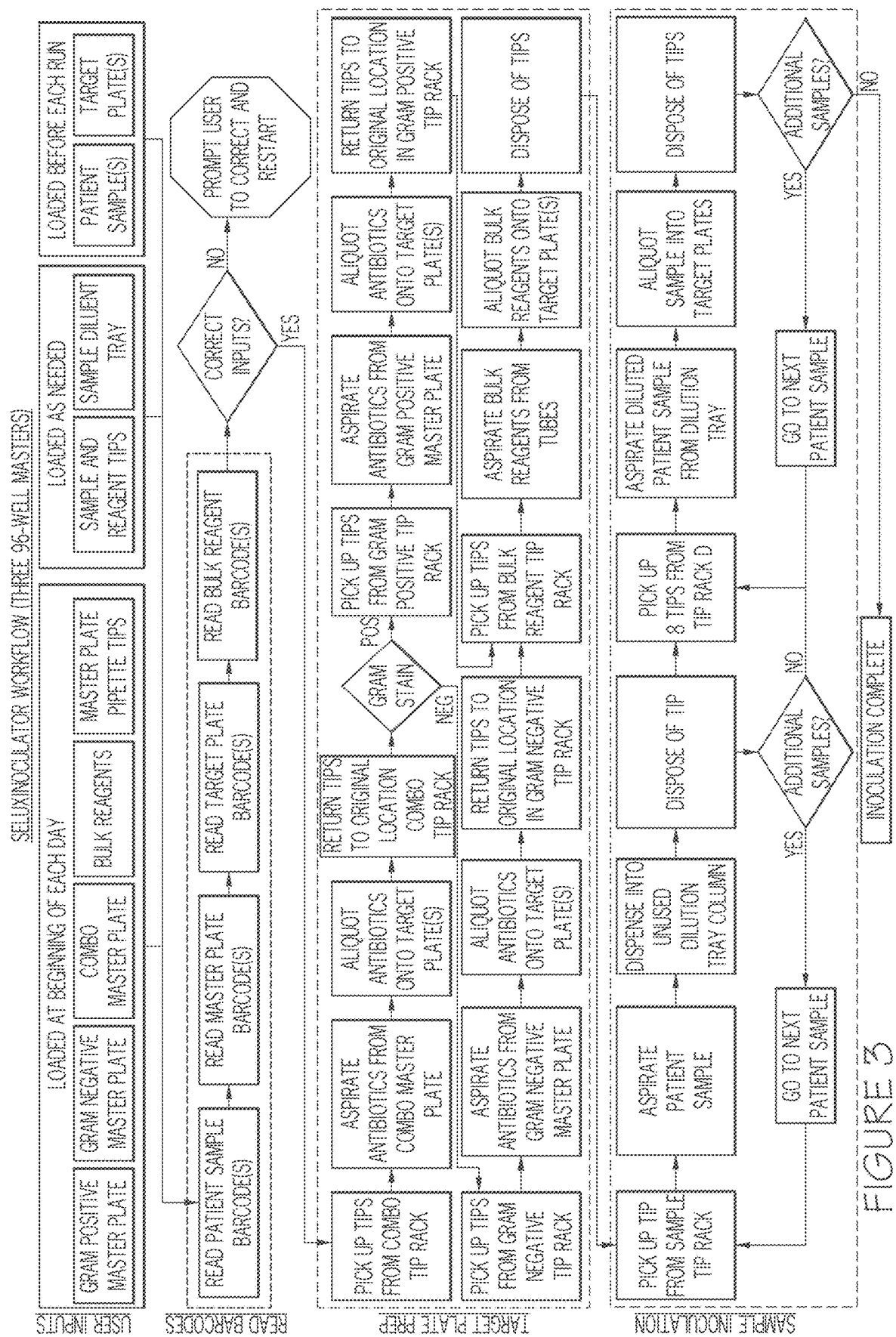
FIG. 3 depicts a schematic diagram of the inoculation workflow for a master cartridge AST assay.

The process of using master cartridges to produce "patient cartridges" or target cartridges in clinical laboratory settings can be automated, using liquid dispensers available from multiple manufacturers, including Hamilton Company, Tecan, Hudson Robotics, etc. A schematic diagram of the inoculation workflow is given in FIG. 3.

First, three master plates are loaded by the user onto chilled plate holders (set to 4° C.). These consist of one Broad Spectrum, one Gram-Positive and one Gram-Negative antibiotic plate. Next the bulk reagents and pipette tips are loaded on tube rack. Master and bulk reagent pipette tips and sample dilution tray are reloaded every 12 samples. For every set of tests, up to four Patient Samples in tubes and up to four 384-well Target Plates (Patient plate) are loaded.

Patient (Target) Plate Preparation.

Antibiotics are transferred from Broad Spectrum Master Plate to Target Plate(s). Antibiotics are "stamped" according to FIG. 10A-B. The inoculator tips should be placed back in the same position of the Broad Spectrum Tip Box for use on subsequent target plates, but should only be used for same antibiotics to avoid cross contamination.

Figure 11A:
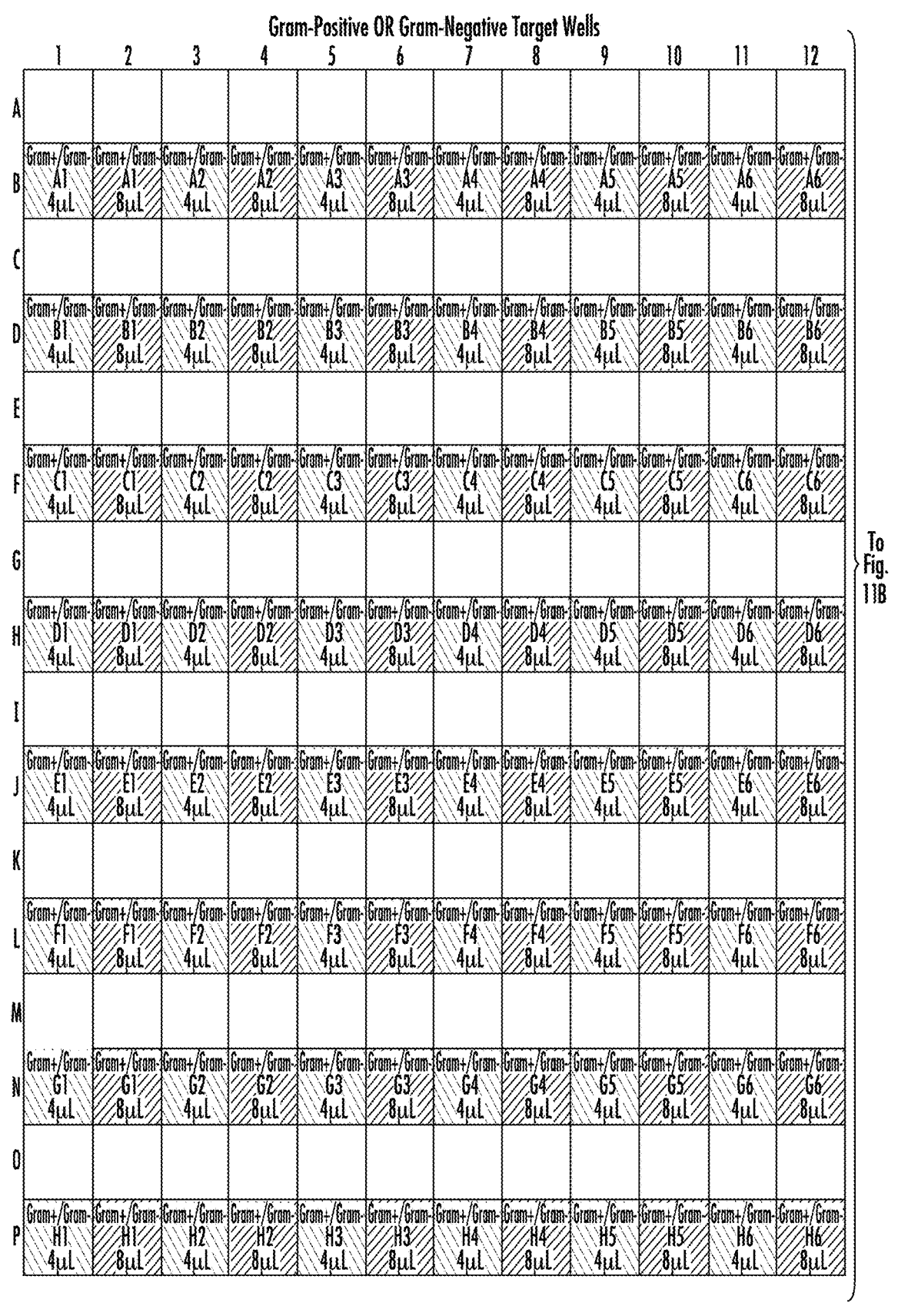
Figure 11B:
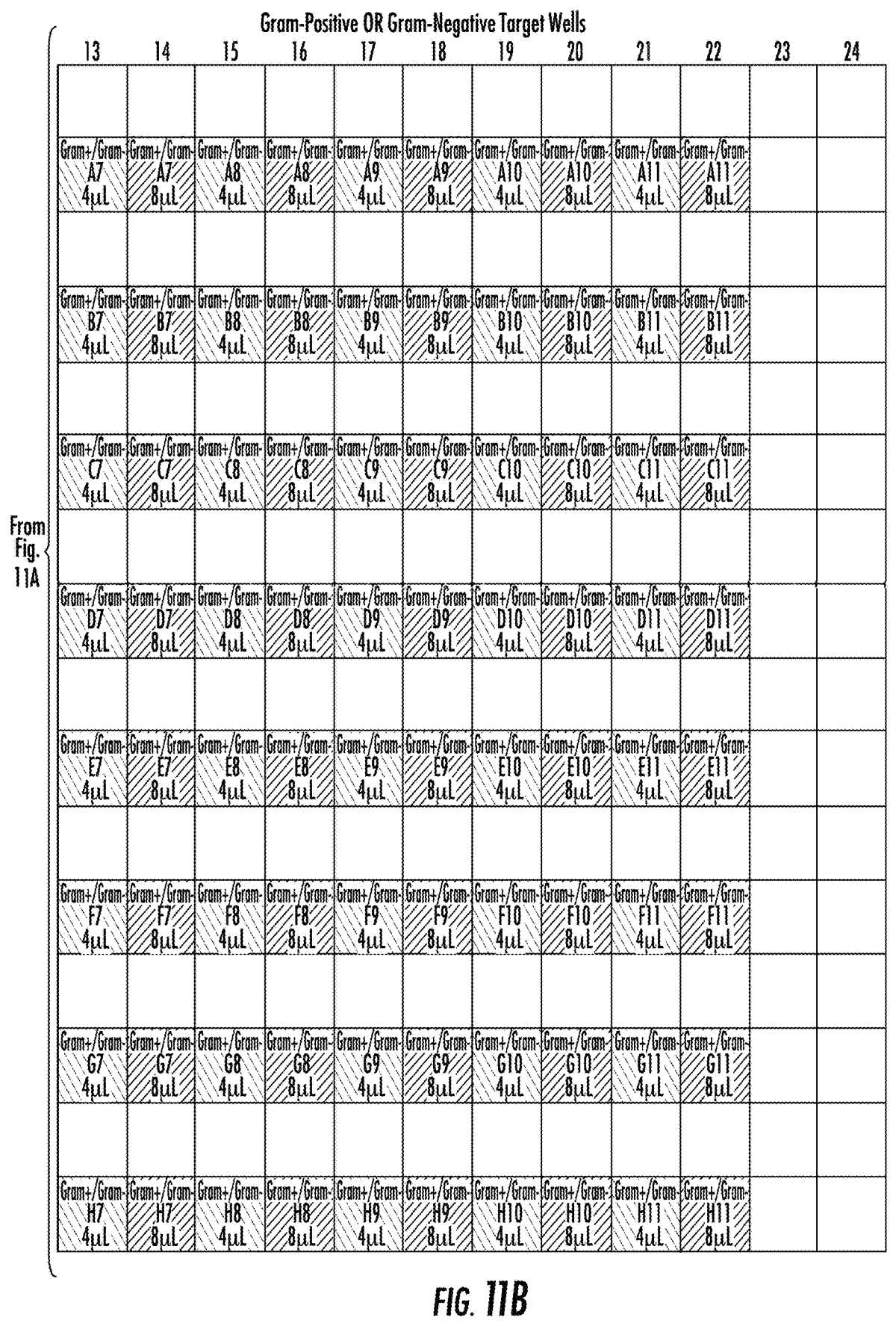

Antimicrobials are transferred from Gram-Positive OR Gram-Negative Master Plate to Target Plate(s) and the antibiotics are "stamped" according to FIG. 11A-B. The inoculator should place tips back in the same position of the correct tip box for use on subsequent target plates. Good care is taken such that any cross contamination is prevented.

Next, the bulk reagents are transferred to Target Plate(s) using Bulk Reagent tips, Target Plates according to Table 5.

Preparation of Patient Sample Dilutions.

Using unused tips from the Sample Tip Box, 2004, of Patient Sample are transferred into an unused column of the Sample Dilution Tray. Used tips should be immediately disposed of to avoid cross contamination. The above steps a repeated for remaining patient samples.

Target Plate Inoculation with Patient Sample.

Using new tips from the Sample Tip Box, 50 μL of diluted patient sample are transferred into Target Plate according to Table Four, this is done with a "jet dispense" to avoid cross contamination. After the Patient Sample has been transferred to each well on the Target Plate, the tips should be disposed of to avoid cross contamination. The above steps are repeated for each additional Patient Sample and Target Plate.

The process can utilize one or more auxiliary cartridges in the machine. Care is taken that the auxiliary cartridges and the master cartridge are not inoculated with microorganisms. Serial dilutions of each antimicrobial compound in performed and dispensed on the sample patient cartridge.

Figure 4:
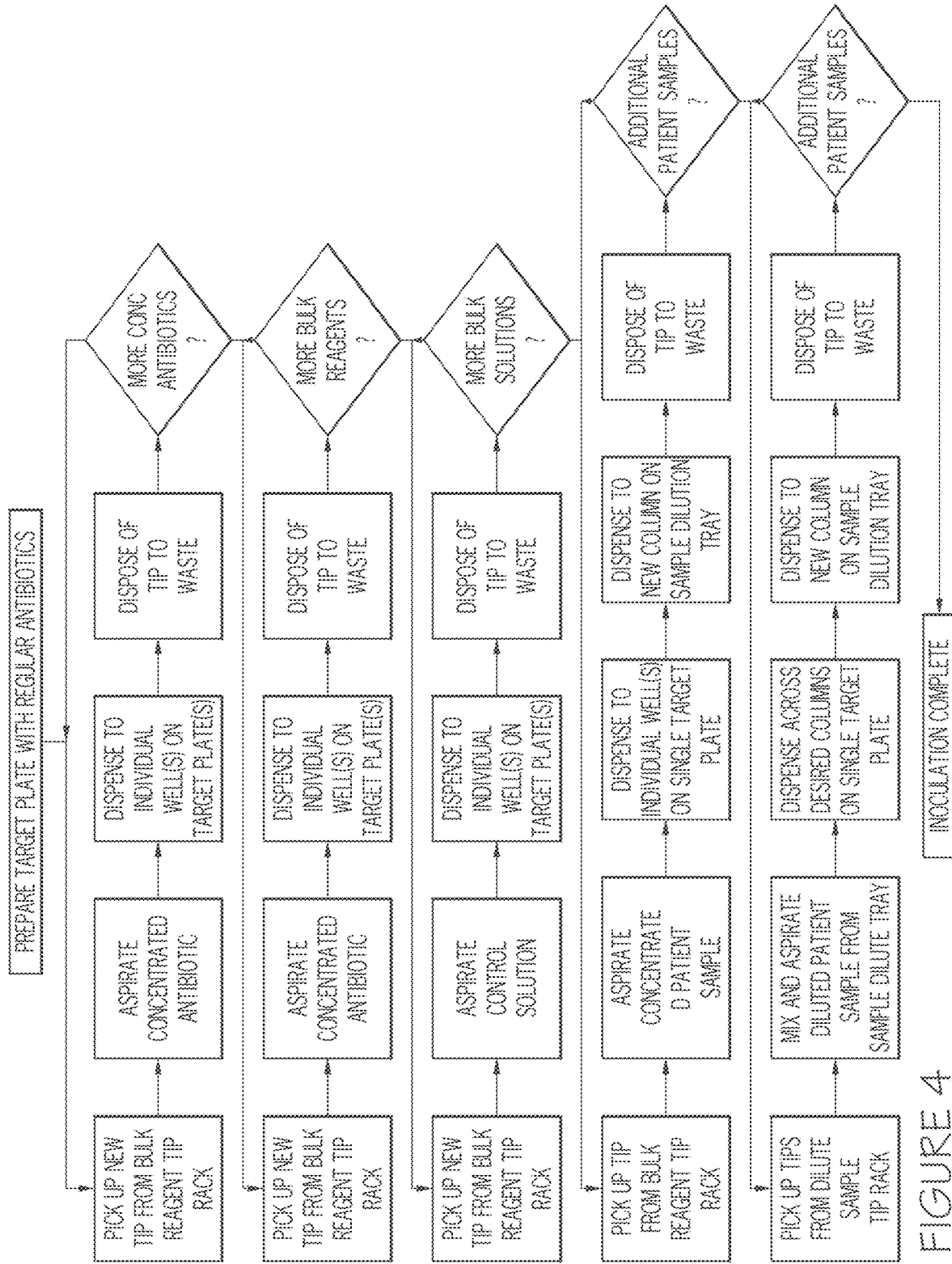
FIG. 4 depicts an individual well flow chart for setting up a patient cartridge from a master cartridge for an AST assay.

A schematic diagram of the individual well flow chart is given in FIG. 4.

The antibiotics shown are vancomycin, daptomycin, ceftaroline and levofloxacin, of which the MICs obtained from the broth microdilution reference method for this strain were 0.5, 0.25, 0.12, and 0.25 μg/ml, respectively. A clinical isolate of *S. aureus* was used. Data represents the TRF signal in RFUs. Graphs in the top row contain data from 384-well plates. Graphs in the bottom row contain data from 96-well plates.

Figure 7:
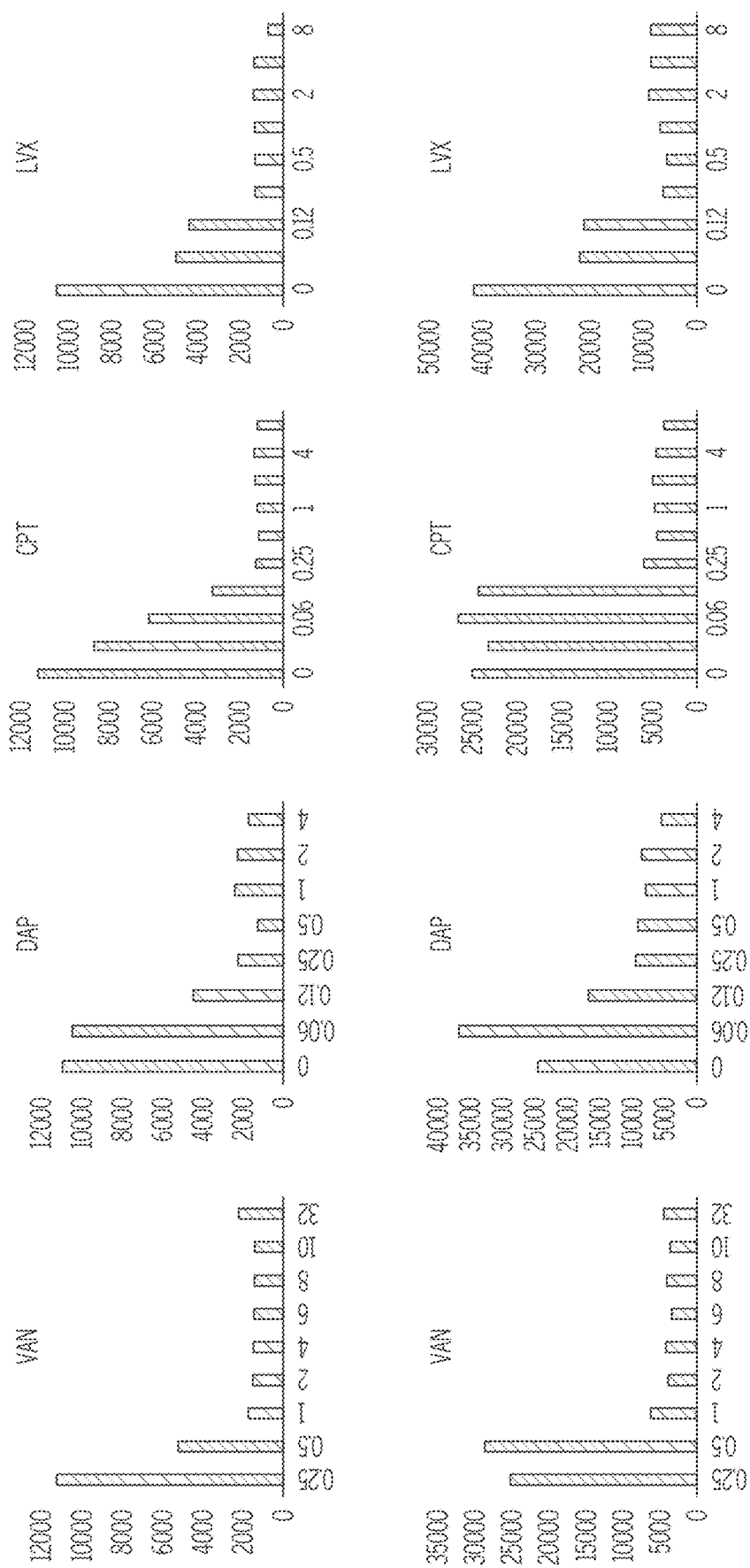
FIG. 7 depicts bacterial growth results showing minimum inhibitory concentration (MIC) values for each antimicrobial. Graphs in the top row contain data from 384-well plates. Graphs in the bottom row contain data from 96-well plates.

Shown in Table 6 and Table 7, MIC results for antimicrobial panels 1 and 2 respectively using a master cartridge format and a 384 well patient cartridge (column 3) agrees reliably with that run by standard 96 well AST assay plate (right hand column). FIG. 7 shows corresponding growth curves determining the MIC values of the antimicrobials on patient sample microbes. This shows that master cartridge with the 384 well plate format offers reliable results, in addition to the other advantages discussed herein.

TABLE 5

Bulk Reagents
T

| | 1 | 2 | 3 | 4 | 5 | 6 | 7 | 8 | 9 | 1 | 1 | 1 | 1 | 1 | 1 | 1 | 1 | 1 | 2 | 2 | 2 | 2 | 2 |
|---|---|---|---|---|---|---|---|---|---|---|---|---|---|---|---|---|---|---|---|---|---|---|---|
| A | | | | | | | | | | | | | | | | | | | | | | | |
| B | | | | | | | | | | | | | | | | | | | | | | | |
| C | | | | | | | | | | | | | | | | | | | | | | | |
| D | | | | | | | | | | | | | | | | | | | | | | B4 | B4 |
| E | | | | | | | | | | | | | | | | | | | | | | B4 | B4 |
| F | | | | | | | | | | | | | | | | | | | | | | | |
| G | | | | | | | | | | | | | | | | | | | | | | | B3 |
| H | | | | | | | | | | | | | | | | | | | | | | | |
| I | | | | | | | | | | | | | | | | | | | | | | | B3 |
| J | | | | | | | | | | | | | | | | | | | | | | | |
| K | | | | | | | | | | | | | | | | | | | | | | | B3 |
| L | | | | | | | | | | | | | | | | | | | | | | | |
| M | | | | | | | | | | | | | | | | | | | | | | | |
| N | | | | | | | | | | | | | | | | | | | | | | B2 | B2 |
| O | | | | | | | | | | | | | | | | | | | | | | B1 | B1 |
| P | | | | | | | | | | | | | | | | | | | | | | B1 | B1 |

Figure 5:
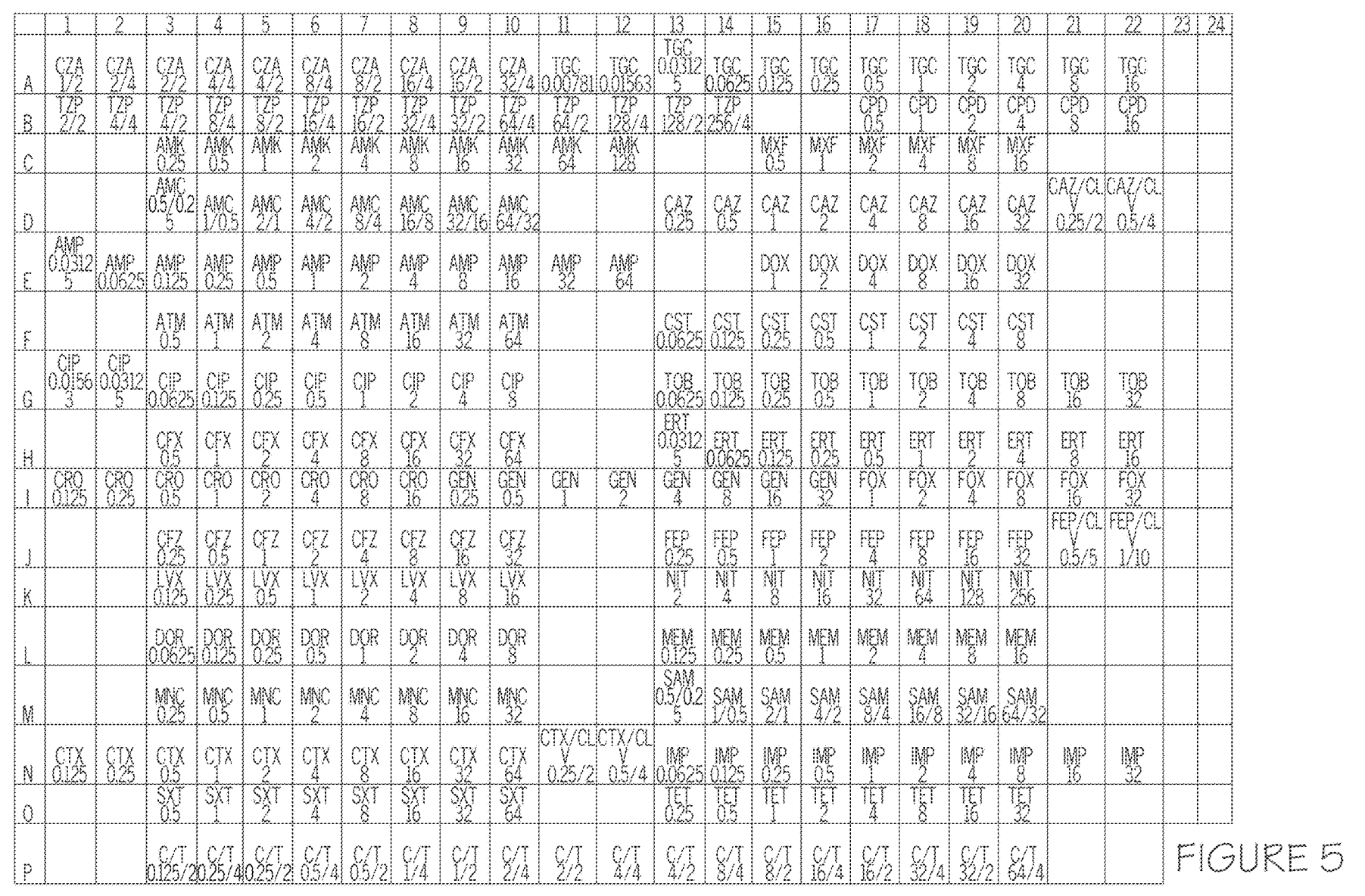
Figure 6:
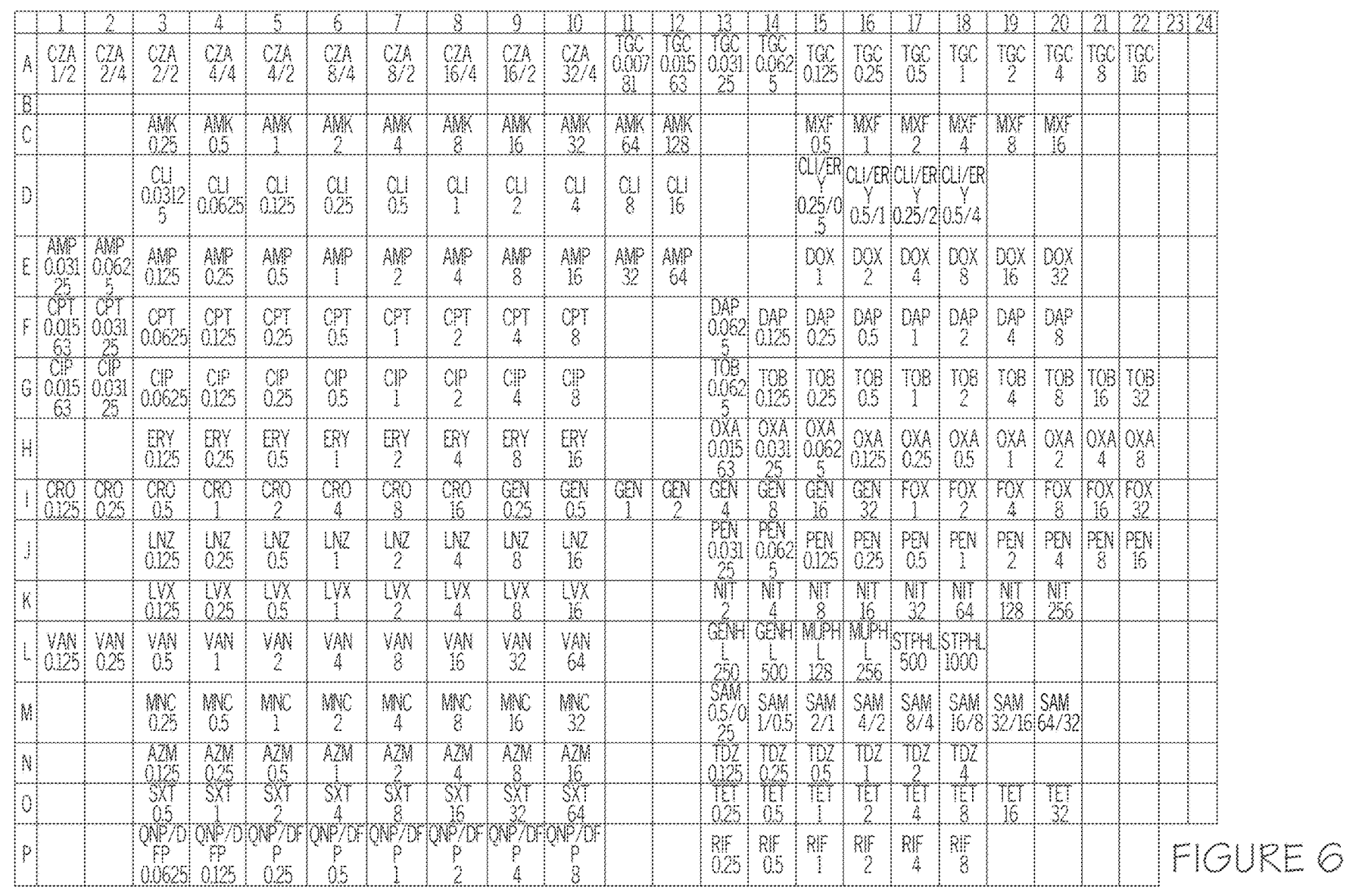

The final layout of a patient cartridge (also referred to as Target Plate) comprising antimicrobials against gram negative bacteria is depicted in FIG. 5. The final layout of a patient cartridge (also referred to as Target Plate) comprising antimicrobials against gram positive bacteria is depicted in FIG. 6.

For testing minimum inhibitory concentration (MIC) the range of serial dilutions of each antimicrobial dispensed is sufficient to cover the MIC over a dynamic range in several orders of magnitude. For qualitative susceptibility testing also, a sufficient dilution range is prepared on the sample patient cartridge, as per CLSI standards. These dilutions may be present in repetition and additional dilutions may be utilized. The concentrations of antimicrobial solutions in the sample patient cartridges are referred to as the "testing concentrations." Testing concentrations represent all concentrations within the ranges for quality control or MIC interpretive criteria for a given antibiotic, as defined by the CLSI M100S Manual.

Example 4. Rapid AST Performed in a 384-Well Plate Provides Similar Data to an Assay Performed in a 96-Well Plate This example demonstrates successful AST assay on 384 well plate yielding high data reliability.

TABLE 6

MIC results for antimicrobial panel 1

| Antibiotic | Quality Control Range | MICs obtained from panel made from Master Plate | MICs obtained from 96-well Antibiotic Panel |
|---|---|---|---|
| Ceftriaxone | 0.03-0.12 | ≤0.125 | ≤0.12 |
| Ceftazidime | 0.06-0.5 | ≤1 | 0.25 |
| Ampicillin-Sulbactam | 2-8 | 8 | 8 |
| Tobramycin | 0.25-1 | 0.5 | 1 |
| Amikacin | 0.5-4 | 4 | 4 |
| Ampicillin | 2-8 | 4 | 8 |
| Piperacillin-tazobactam | 1-4 | ≤1 | 4 |
| Levofloxacin | 0.008-0.06 | ≤0.25 | ≤0.06 |
| Cefepime | 0.015-0.12 | ≤0.25 | ≤0.03 |

TABLE 7

MIC results for antimicrobial panel 2

| Antibiotic | Quality Control Range | MICs obtained from panel made from Master Plate | MICs obtained from 96-well Antibiotic Panel |
|---|---|---|---|
| Linezolid | 1-4 | 2 | 2 |
| Ceftaroline | 0.12-0.5 | 0.5 | 0.25 |

TABLE 7-continued

MIC results for antimicrobial panel 2

| Antibiotic | Quality Control Range | MICs obtained from panel made from Master Plate | MICs obtained from 96-well Antibiotic Panel |
|---|---|---|---|
| Tedizolid | 0.25-1 | 0.25 | 0.5 |
| Oxacillin | 0.12-0.5 | 0.5 | 0.5 |
| Rifampin | 0.004-0.015 | ≤0.25 | 0.004 |
| Ceftriaxone | 1-8 | 2 | 4 |
| Ceftazidime | 4-16 | 4 | 8 |
| Ampicillin | 0.5-2 | 1 | 1 |
| Levofloxacin | 0.06-0.5 | ≤0.25 | 0.25 |

Example 5. Non-Uniform Volume Loss Detected in 384-Well Plates

Figure 8:
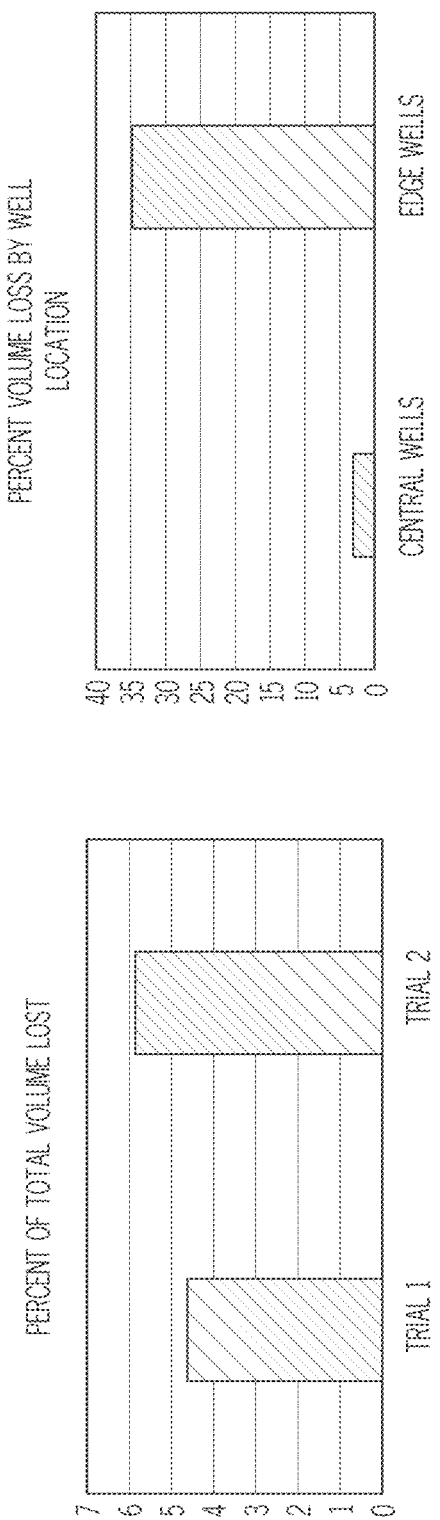
FIG. 8 depicts percentage of volume losses during an AST assay in 384-well plates from two different experiments (left panel) and from central vs. edge wells on the 384-well plate (right panel).

In order to test the rate of evaporation at various regions of the plate, 40 µl of water were added to each well in a 384-well plate. Plate masses were recorded and plates with lids were incubated shaking at 35° C., 150 rpm (Southwest Science Mini IncuShaker) overnight for approximately 18 hours. After incubation, plates were masses to determine total volume loss during incubation (FIG. 8, left panel). This data records the total loss of liquid volume on the entire plate. To determine the volume remaining in individual wells, micropipettes were used. The average percent loss of volume in at least 6 central or edge wells is reported (FIG. 8 right panel). This data indicates that the loss of liquid volume was non-uniform throughout the plate, with the wells in the periphery losing about 6 times more liquid volume than the ones in the center.

Example 6. Single-Cartridge Quality Control Panel Designs

The inventors have devised 384-well AST cartridge designs that can be used both for AST testing of patient samples using a panel of antimicrobials and, when loaded with QC organisms specified for the antimicrobials in the panel, to provide quality control for the AST panel on the cartridge. Exemplary cartridge layouts specific for gram positive and gram negative microbes are presented in FIG. 2B and FIG. 2C respectively. In these figures, rows and columns of the cassette are indicated at the left-hand and top margins. Wells are grouped together by three-letter antimicrobial codes as set forth in Table 8, below and by the QC organisms indicated for each grouping. The concentration of each antimicrobial is indicated for each well within a grouping in µg/mL.

TABLE 8 three-letter antimicrobial codes for FIGS. 2B, 2C, 2D, and 2E

| Antimicrobial | Abbreviation | Antimicrobial | Abbreviation |
|---|---|---|---|
| Ampicillin | AMP | Amikacin | AMK |
| Azithromycin | AZM | Amoxicillin-Clavulanic Acid | AMC |
| Cefoxitin Screen | FOX SCN | Ampicillin | AMP |
| Ceftaroline | CPT | Ampicillin-Sulbactam | SAM |
| Ciprofloxacin | CIP | Aztreonam | ATM |
| Clarithromycin | CLR | Cefazolin | CFZ |
| Clindamycin | CLI | Cefepime-Zidebactam | FPZ |
| Daptomycin | DAP | Cefotaxime | CTX |
| Delafloxacin | DFX | Cefoxitin | FOX |
| Doxycline | DOX | Cefpodoxime | CPD |
| D-Test (Cli/Ery) | DTEST | Ceftaroline | CPT |
| Eravacycline | ERV | Ceftazidime | CAZ |
| Erythromycin | ERY | Ceftazidime-Avibactam | CCA |
| Gentamicin | GEN | Ceftolozane-Tazobactam | C/T |
| Gentamicin High Level | GEN HL | Ceftriaxone | CRO |
| Iclaprim | ICL | Cefuroxime | CXM |
| Levofloxacin | LVX | Ciprofloxacin | CIP |
| Linezolid | LNZ | Colistin | CST |
| Minocycline | MIN | Doripenem | DOR |
| Moxifloxacin | MXF | Doxycycline | DOX |
| Mupirocin High Level | MUP HL | Eravacycline | ERV |
| Nitrofurantoin | NIT | Ertapenem | ERT |
| Norfloxacin | NOR | ESBL-1 (Cefepime/Clav) | FEP/CLV |
| Ofloxacin | OFX | ESBL-2 (Cefotaxime/Clav) | CTX/CLV |
| Oxacillin | OXA | ESBL-3 (Ceftazidime/Clav) | CAZ/CLV |
| Penicillin | PEN | Gentamicin | GEN |
| Plazomicin | PLZ | Imipenem | IMP |
| Rifampin | RIF | Meropenem | MEM |
| Streptomycin High Level | STP HL | Meropenem-Vaborbactam | MEV |
| Sulfa-Trimeth | SXT | Minocycline | MIN |
| Synercid | SYN | Moxifloxacin | MXF |
| Tedizolid | TDZ | Nitrofurantoin | NIT |
| Telithromicin | TEL | Norfloxacin | NOR |
| Tetracycline | TET | Ofloxacin | OFX |
| Tigecycline | TIG | Omadacycline | OMA |
| Vancomycin | VAN | Piperacillin-Tazobactam | TZP |
| Amoxicillin | AMX | Plazomicin | PLZ |
| Cefepime | FEP | Sulfamethoxazole-Trimethoprim | SXT |
| Imipenem-Relebactam | IRB | Tetracycline | TET |
| Ceftazidime-Tazobactam | CAZ-Taz | Tigecycline | TIG |
| Ceftazidime-Avibactam | CZA | Tobramicin | TOB |
| Clindamycin-induced Erythromycin resistance (screening test) | CLI/ERY | Trimethoprim | TMP |
| Tedizolid | TZD | Aztreonam-Avibactam | AZA |

As the figures indicate, a single cartridge according to an embodiment of this disclosure includes, for each antimicrobial in an AST panel, a plurality of wells comprising the antimicrobial at various concentrations across a testing and QC range. Those of skill in the art will appreciate that the MIC range of an antimicrobial for a patient sample may not be identical, or even overlapping with, a MIC range of the antimicrobial for a quality control organism, and that the dilution ranges for antimicrobials in cartridges according to this disclosure will not necessarily match the ranges used in other AST cartridge designs.

Figure 2B:
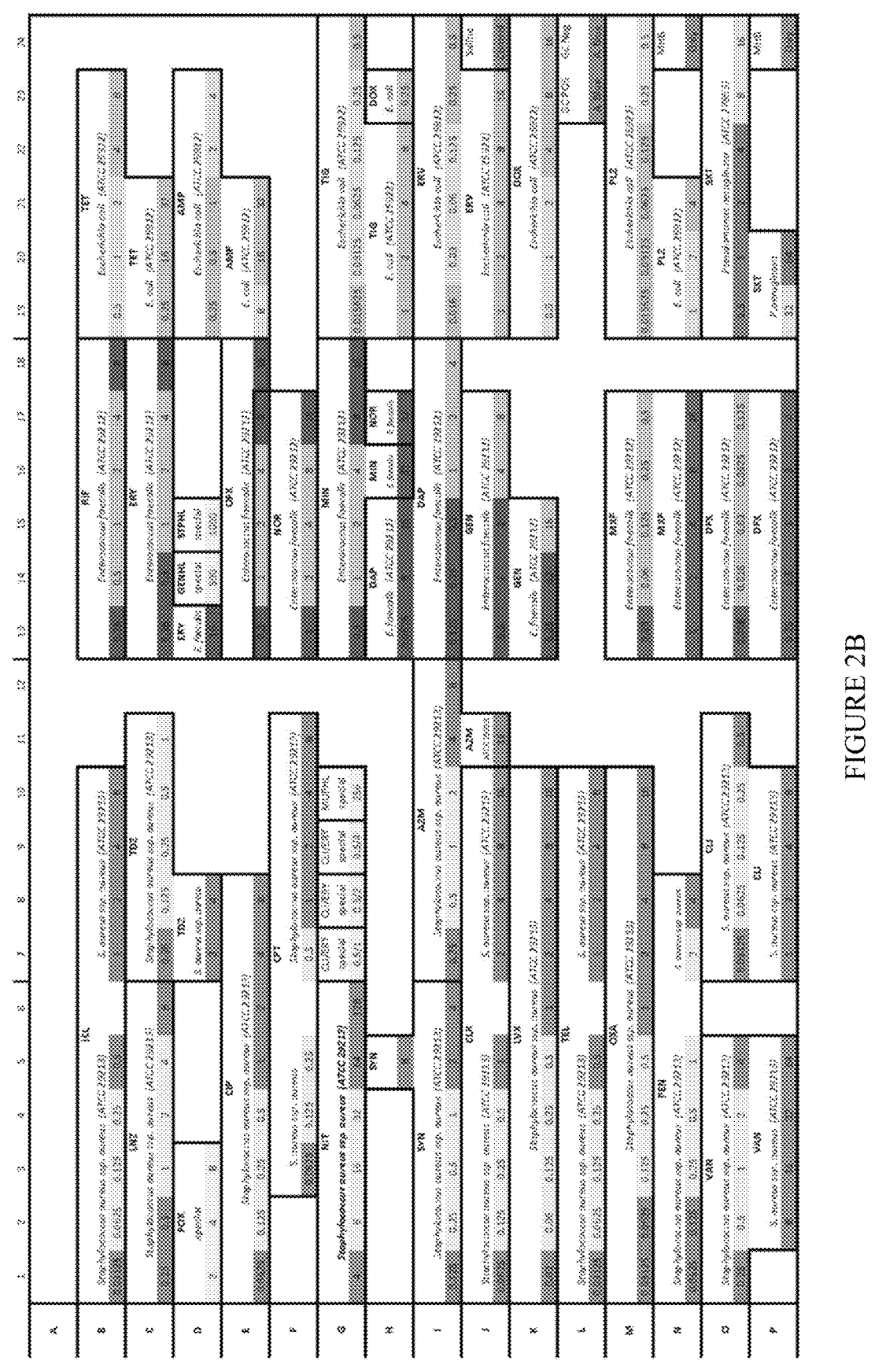
Figure 2C:
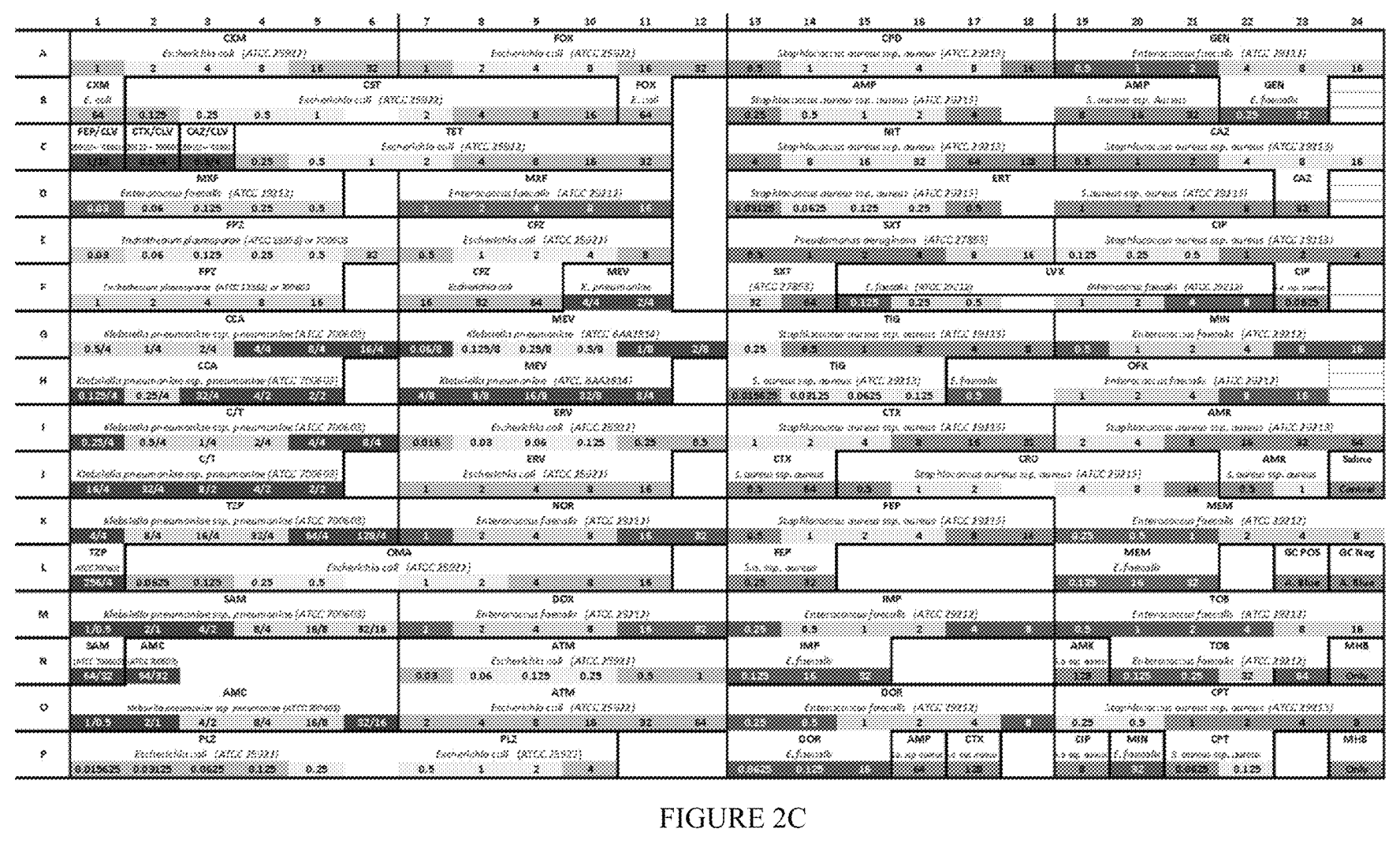

The AST panels according to the embodiments exemplified in FIGS. 2B and 2C constitute panels of 36 antimicrobials for gram-positive bacteria and 41 antimicrobials for gram-negative bacteria. These plates are further sufficient to enable multiple quality control organisms to be processed simultaneously. It should be noted that current AST panels are most often implemented on 64, 96, or 132 well plates, and most AST panels include fewer than 20 different antimicrobials, and that the designs described herein expand the number of antimicrobials that can be tested on a single AST cartridge during a single run. In the cartridge designs exemplified in FIGS. 2B and 2C, dilution series for antimicrobials utilizing the same QC organism are generally clustered along the same axis rather than randomly, which facilitates loading and processing of multiple quality control organisms in a single run.

The inventors have devised 384-well AST cartridge designs that can be used both for AST testing of patient samples using a panel of antimicrobials and, when loaded with QC organisms specified for the antimicrobials in the panel, to provide quality control for the AST panel on the cartridge. Exemplary cartridge layouts specific for gram positive and gram negative microbes are presented in FIG. 2D and FIG. 2E respectively. In these figures, rows and columns of the cassette are indicated at the left-hand and top margins. Wells are grouped together by three-letter antimicrobial codes as set forth in Table 8, and by the QC organisms indicated for each grouping. The concentration of each antimicrobial is indicated for each well within a grouping in μg/mL.

Figure 2D:
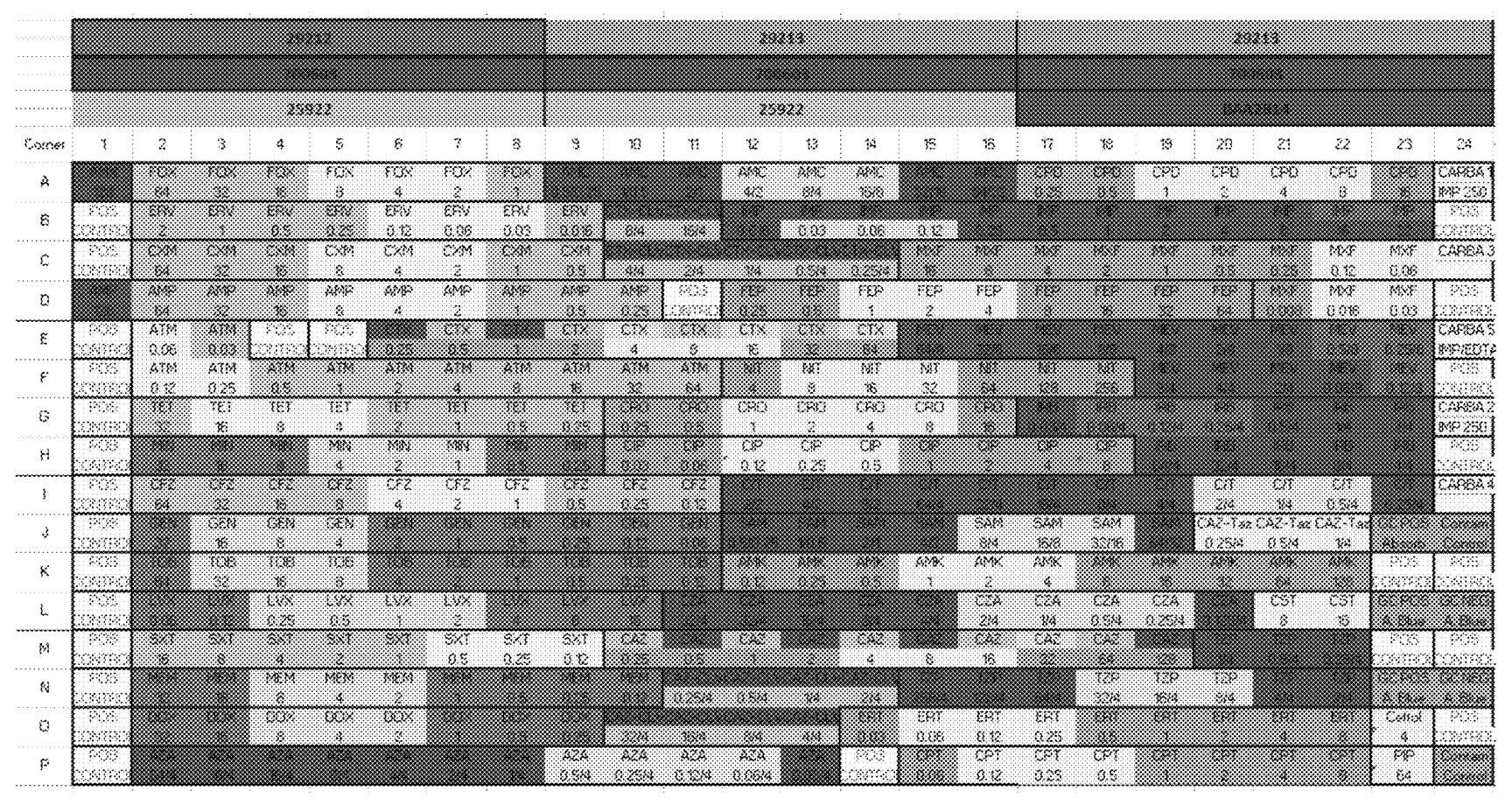
Figure 2E:
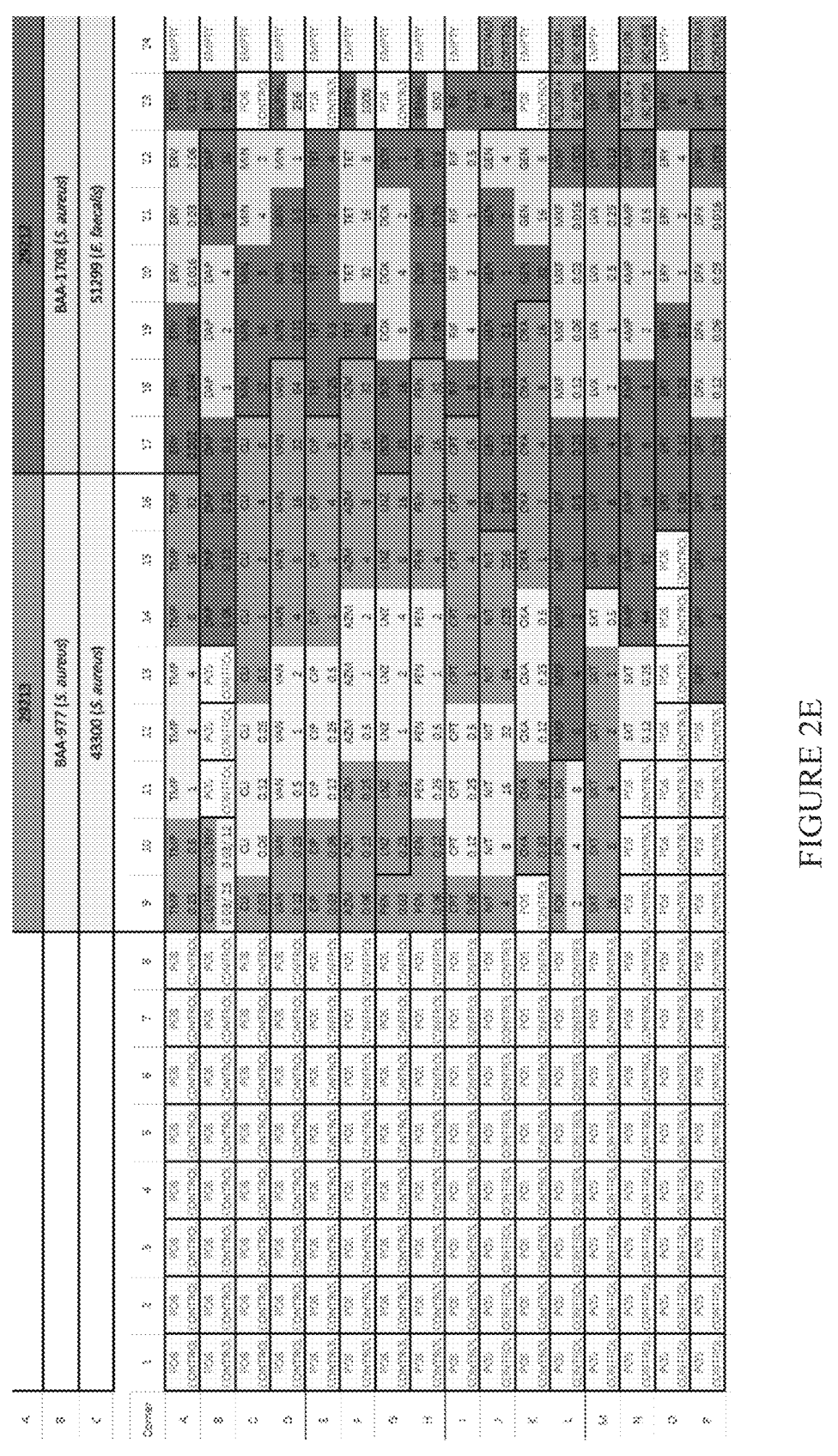

The AST panels according to the embodiments exemplified in FIGS. 2D and 2E constitute panels of about 23 antimicrobials plus 5 screening test for gram-positive bacteria and about 34 antimicrobials plus 1 screening test for gram-negative bacteria. These panels are further sufficient to enable multiple quality control organisms to be processed simultaneously. In particular, the dilution range for QC may be a subset of the complete dilution range on the panel for some antibiotics. Exemplary panel layouts demonstrating this design are shown in FIG. 2D and FIG. 2E. In these layouts, the 24 columns of reservoirs on each panel are divided into three regions of 8 columns each. These are termed "QC blocks" because each may be inoculated with a different QC organism for QC testing, though each plate will be inoculated with the same organism for clinical isolate testing. Each plate (gram-negative and gram-positive) requires three different QC runs, labeled QC-1 to QC-3 in FIGS. 2D and 2E. The QC organisms that should be run in each block for each run QC-1 to QC-3 are shown in FIGS. 2D and 2E in the appropriate row.

In the preferred embodiment, the system software directs the user to select whether a clinical or QC sample is to be tested. If a clinical sample is to be tested, the user may be further directed to select whether a comprehensive or multiplex test should be performed. If the user selects a comprehensive test, the user interface (UI) will direct her/him to prepare an inoculum tube of the sample and load this and the appropriate comprehensive panel into the carrier. The screen capture in FIG. 3A shows the UI during active loading of a second, gram-positive panel in a 4-panel carrier during the step where the user is preparing the inoculum sample tube and loading the panel into the carrier. If a user instead selects from the UI to perform QC on a comprehensive panel, the system directs her/him to use a multiplex carrier and prepare inoculum sample tubes of the appropriate QC organisms, as shown in the screen capture in FIG. 3B. Note this example shows the run labeled "QC-2" in FIG. 2E.

In some embodiments one or more antimicrobial dilutions may be present that are necessary for QC but do not directly support the determination of an MIC or screening test result for a sample under test. For example, in FIG. 2E, AMX is present in order to provide a confirmatory result for QC to indicate that ATCC 700603 retains resistance to AMX, which is necessary in order to use this QC organism to perform QC on AMC.

It should be noted that current AST panels are most often implemented on 64, 96, or 132 well plates, and most AST panels include fewer than 20 different antimicrobials, and that the designs described herein expand the number of antimicrobials that can be tested on a single AST cartridge during a single run. It should also be noted that the invention described here requires no differences be made in panel concentrations when used for sample testing or QC, important for achieving low-cost consumables.

In the cartridge designs exemplified in FIGS. 2D and 2E, dilution series for antimicrobials utilizing the same QC organism are generally clustered along the same axis rather than randomly, which facilitates loading and processing of multiple quality control organisms in a single run. In particular, this may speed inoculation. In FIGS. 2D and 2E, the dilution series are oriented horizontally. The dilution series are oriented in the same direction such that the inoculation of the cartridge with the patient derived sample does not cause contamination within the cartridge. This orientation allows for complex AST panels that can contain a multitude of antimicrobials. Using current AST panels, it is laborious and expensive to provide QC for the entire panel because of the number of panels that must be tested. The method of this disclosure allows for QC testing which uses far fewer materials and may take less time.

Cartridges according to the embodiments of this disclosure are generally, but not necessarily, adapted for use in AST systems as described in US pre-grant publication no. 2018/0088141 by Vacic, et al. ("Vacic"), which is incorporated by reference for all purposes. More particularly, paragraphs 73-74 describe an AST method comprising a first step of checking a control well or wells of a cartridge for sufficient growth of microbes in the sample and, once it is determined that sufficient growth has occurred, conducting one or more endpoint assays to assess the growth microbes under conditions of different antimicrobials at different concentrations. Thus, in certain embodiments the cartridge includes one or more wells that do not include an antimicrobial and may be used for sufficient growth assays. In normal, AST testing operation, the wells of the cartridge are loaded with a sample and incubated; the sufficient growth well or wells are tested at a predetermined interval (e.g., 0.5, 1, 2, 3, 4 etc. hours) and, once sufficient growth is identified, one or ore endpoint assays are performed as described in Vacic.

For QC use, each of the one or more sufficient growth wells of the cartridge receives a quality control organism rather than a patient sample, e.g., at least one sufficient growth well can receive a quality control organism that is specified for each of the antimicrobials on the cartridge, e.g., as listed in FIGS. 2B and C. The sufficient growth wells may be evaluated after a set interval, e.g., 0.5, 1, 2, 3, or 4, hours, and, in some cases, after sufficient growth is determined for a QC organism, endpoint testing is initiated for the wells receiving that QC organism; the remaining sufficient growth wells are examined for sufficient growth and, as each QC organism is determined to have reached a significant growth threshold, endpoint testing for the wells containing that QC organism is initiated. Alternatively, endpoint assay testing may be performed on the cartridge only after multiple QC organisms have reached a sufficient growth threshold; or, where QC organisms are expected to have similar growth kinetics, endpoint testing may be initiated after a predetermined growth interval and confirmed growth of a single QC organism.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims.

What is claimed is:

1. A cartridge for performing antimicrobial susceptibility testing of microorganisms, comprising:
a plurality of reservoirs arranged in a series of rows and columns, each reservoir containing an antimicrobial agent; and
a plurality of reservoir sets, each reservoir set comprising a series of adjacent reservoirs along a row of the cartridge and comprising a dilution series of the same antimicrobial agent;
wherein the columns of reservoirs within the cartridge are divided into at least two regions, wherein each region comprises a group of columns for receiving a quality control organism that is different from a quality control organism received by a different region, and each region has at least two reservoir sets for assessing the antimicrobial susceptibility of the quality control organism received in that region;
wherein the reservoir sets within each region comprise different antimicrobial agents from each other; and
wherein the cassette is adapted to receive a patient sample or first and second quality control organisms, the first quality control organism being applied to a reservoir set within a first region of the at least two regions, and the second quality control organism being applied to a reservoir within a second region of the at least two regions.

2. The cartridge of claim 1, wherein each column region comprises at least four reservoir sets.

3. The cartridge of claim 1, wherein each column region comprises at least eight reservoir sets.

4. The cartridge of claim 1, comprising at least 384 reservoirs.

5. The cartridge of claim 1, wherein each dilution series comprises sufficient dilution extents to include a minimum inhibitory concentration of a quality control organism applied to that dilution series.

6. The cartridge of claim 1, wherein two or more reservoirs of the cartridge comprise a sufficient quantity of an antimicrobial agent to inhibit the growth of a plurality of gram-negative microorganisms.

7. The cartridge of claim 1, in which one or more of the antimicrobial agents is selected from the group consisting of Amikacin, Amikacin-fosfomycin, Amoxicillin, Amoxicillin-clavulanate, Ampicillin, Ampicillin-sulbactam, Azithromycin, Azithromycin-Avibactam, Azlocillin, Aztreonam, Aztreonam-avibactam, Besifloxacin, Biapenem, Cadazolid, Carbenicillin, Cefaclor, Cefamandole, Cefazolin, Cefdinir, Cefditoren, Cefepime, Cefepime-tazobactam, Cefetamet, Cefiderocol, Cefixime, Cefmetazole, Cefonicid, Cefoperazone, Cefotaxime, Cefotetan, Cefoxitin, Ceftolozane-tazobactam, Cefpodoxime, Cefprozil, Ceftaroline, Ceftaroline-avibactam, Ceftazidime, Ceftazidime-avibactam, Ceftibuten, Ceftizoxime, Ceftobiprole, Ceftolozane-tazobactam, Ceftriaxone, Cefuroxime, Cephalothin, Chloramphenicol, Cinoxacin, Ciprofloxacin, Clarithromycin, Clinafloxacin, Clindamycin, Colistin, Dalbavancin, Daptomycin, Delafloxacin, Dirithromycin, Doripenem, Doxycycline, Enoxacin, Eravacycline, Ertapenem, Erythromycin, Faropenem, Fidaxomicin, Finafloxacin, Fleroxacin, Fosfomycin, Fusidic acid, Garenoxacin, Gatifloxacin, Gemifloxacin, Gentamicin, Gepotidacin, Grepafloxacin, Iclaprim, Imipenem, Imipenem-Relebactam, Kanamycin, Lefamulin, Levofloxacin, Levonadifloxacin, Linezolid, Linopristin-flopristin, Lomefloxacin, Loracarbef, Mecillinam, Meropenem, Methicillin, Mezlocillin, Minocycline, Moxalactam, Moxifloxacin, Nafcillin, Nalidixic acid, Netilmicin, Nitrofurantoin, Norfloxacin, Ofloxacin, Omadacycline, Oritavancin, Oxacillin, Penicillin, Piperacillin, Piperacillin-tazobactam, Plazomicin, Polymyxin B, Quinupristin-dalfopristin, Razupenem, Rifampin, Solithromycin, Sparfloxacin, Sulfisoxazole, Sulopenem, Tedizolid, Teicoplanin, Televancin, Telithromycin, Tetracycline, Ticarcillin, Ticarcillin-clavulanate, Tigecycline, Tobramycin, Trimethoprim, Trimethoprim-sulfamethoxazole, Trospectomycin, Vancomycin, Aculeacin A, Amphotericin B, Caspofungin, Clotrimazole, Fluconazole, Flucytosine, 5-Fluorocytosine, Griseofulvin, Itraconazole, Ketoconazole, Nystatin, Sordarin, Terbinafine, Vaborbactam-meropenem, Voriconazole and a salt or hydrate form thereof.

8. The cartridge of claim 1, wherein one or more quality control organisms is selected from the group consisting of *Staphylococcus aureus* ssp. *aureus* (ATCC 29213); *Enterococcus faecalis* (ATCC 29212);
*Escherichia coli* (ATCC 25922);
*Klebsiella pneumoniae* ssp. *pneumoniae* (ATCC 700603);
*Klebsiella pneumoniae* (ATCC BAA2814);
*Pseudomonas aeruginosa* (ATCC 27853); *E. faecalis* (ATCC 51299); *S. aureus* (BAA-1708); *S. aureus* (BAA-977); *S. aureus* (ATCC 43300); *Streptococcus pneumoniae* (ATCC 49619) and *Trichothecium plasmoparae* (ATCC 13353).

9. The cartridge of claim 1, wherein each dilution series is replicated two or more times on the cartridge, and the cartridge is inoculated with two or more patient samples.

10. The cartridge of claim 1, wherein the cartridge is inoculated with a patient sample comprising a gram-negative microorganism, and at least two reservoirs in the cartridge are inoculated at a higher concentration than the other reservoirs in the cartridge.

11. A kit for performing antimicrobial susceptibility testing (AST), comprising:
a cartridge according to claim 1; and
instructions for performing:
(a) an AST method comprising the steps of:
inoculating the cartridge with a patient sample; and
assessing, based on a comparison of cell growth in differing antimicrobial concentrations, one of a minimum inhibitory concentration of an antimicrobial agent, and a susceptibility to an antimicrobial agent; and
(b) a quality control method comprising the steps of:
inoculating the cartridge with at least one quality control organism specified for an antimicrobial agent present on the cartridge; and
assessing, based on a comparison of cell growth in differing antimicrobial concentrations and a normal range for the quality control organism, whether a minimum inhibitory concentration of an antimicrobial agent is within the normal range for the quality control organism.

12. The kit of claim 11, wherein the quality control method comprises the step of simultaneously applying the first and second quality control organism to the cartridge.

13. The kit of claim 11, wherein each column region comprises at least four reservoir sets.

14. The kit of claim 11, wherein each column region comprises at least eight reservoir sets.

15. The kit of claim 11, wherein the cassette comprises at least 384 reservoirs.

16. The kit of claim 11, wherein each dilution series comprises sufficient dilution extents to include a minimum inhibitory concentration of a quality control organism applied to that dilution series.

17. The kit of claim 11, wherein two or more reservoirs of the cartridge comprise a sufficient quantity of an antimicrobial agent to inhibit the growth of a plurality of gram-negative microorganisms.

18. The kit of claim 11, in which one or more of the antimicrobial agents are selected from the group consisting of Amikacin, Amikacin-fosfomycin, Amoxicillin, Amoxicillin-clavulanate, Ampicillin, Ampicillin-sulbactam, Azithromycin, Azithromycin-Avibactam, Azlocillin, Aztreonam, Aztreonam-avibactam, Besifloxacin, Biapenem, Cadazolid, Carbenicillin, Cefaclor, Cefamandole, Cefazolin, Cefdinir, Cefditoren, Cefepime, Cefepime-tazobactam, Cefetamet, Cefiderocol, Cefixime, Cefmetazole, Cefonicid, Cefoperazone, Cefotaxime, Cefotetan, Cefoxitin, Ceftolozane-tazobactam, Cefpodoxime, Cefprozil, Ceftaroline, Ceftaroline-avibactam, Ceftazidime, Ceftazidime-avibactam, Ceftibuten, Ceftizoxime, Ceftobiprole, Ceftolozane-tazobactam, Ceftriaxone, Cefuroxime, Cephalothin, Chloramphenicol, Cinoxacin, Ciprofloxacin, Clarithromycin, Clinafloxacin, Clindamycin, Colistin, Dalbavancin, Daptomycin, Delafloxacin, Dirithromycin, Doripenem, Doxycycline, Enoxacin, Eravacycline, Ertapenem, Erythromycin, Faropenem, Fidaxomicin, Finafloxacin, Fleroxacin, Fosfomycin, Fusidic acid, Garenoxacin, Gatifloxacin, Gemifloxacin, Gentamicin, Gepotidacin, Grepafloxacin, Iclaprim, Imipenem, Imipenem-Relebactam, Kanamycin, Lefamulin, Levofloxacin, Levonadifloxacin, Linezolid, Linopristin-flopristin, Lomefloxacin, Loracarbef, Mecillinam, Meropenem, Methicillin, Mezlocillin, Minocycline, Moxalactam, Moxifloxacin, Nafcillin, Nalidixic acid, Netilmicin, Nitrofurantoin, Norfloxacin, Ofloxacin, Omadacycline, Oritavancin, Oxacillin, Penicillin, Piperacillin, Piperacillin-tazobactam, Plazomicin, Polymyxin B, Quinupristin-dalfopristin, Razupenem, Rifampin, Solithromycin, Sparfloxacin, Sulfisoxazole, Sulopenem, Tedizolid, Teicoplanin, Televancin, Telithromycin, Tetracycline, Ticarcillin, Ticarcillin-clavulanate, Tigecycline, Tobramycin, Trimethoprim, Trimethoprim-sulfamethoxazole, Trospectomycin, Vancomycin, Aculeacin A, Amphotericin B, Caspofungin, Clotrimazole, Fluconazole, Flucytosine, 5-Fluorocytosine, Griseofulvin, Itraconazole, Ketoconazole, Nystatin, Sordarin, Terbinafine, Vaborbactam-meropenem, Voriconazole and a salt or hydrate form thereof.

19. The kit of claim 11, wherein one or more quality control organisms are selected from the group consisting of *Staphylococcus aureus* ssp. *aureus* (ATCC 29213); *Enterococcus faecalis* (ATCC 29212);
*Escherichia coli* (ATCC 25922);
*Klebsiella pneumoniae* ssp. *pneumoniae* (ATCC 700603);
*Klebsiella pneumoniae* (ATCC BAA2814);
*Pseudomonas aeruginosa* (ATCC 27853); *E. faecalis* (ATCC 51299); *S. aureus* (BAA-1708); *S. aureus* (BAA-977); *S. aureus* (ATCC 43300); *Streptococcus pneumoniae* (ATCC 49619) and *Trichothecium plasmoparae* (ATCC 13353).

20. The kit of claim 11, wherein each dilution series is replicated two or more times on the cartridge, and the cartridge is inoculated with two or more patient samples.

21. The kit of claim 11, wherein the cartridge is inoculated with a patient sample comprising a gram-negative microorganism, and at least two reservoirs in the cartridge are inoculated at a higher concentration than the other reservoirs in the cartridge.

* * * * *